US008486959B2

(12) United States Patent
Lee et al.

(10) Patent No.: US 8,486,959 B2

(45) Date of Patent: Jul. 16, 2013

(54) DIBENZO[F,H]ISOQUINOLINE DERIVATIVES

(75) Inventors: Shiow-Ju Lee, Tainan (TW); Cheng-Wei Yang, Kaohsiung (TW); Yue-Zhi Lee, Miaoli County (TW); Yu-Sheng Chao, Monmouth Junction, NJ (US)

(73) Assignee: National Health Research Institutes, Miaoli County (TW)

( * ) Notice: Subject to any disclaimer, the term of this patent is extended or adjusted under 35 U.S.C. 154(b) by 248 days.

(21) Appl. No.: 13/006,563

(22) Filed: Jan. 14, 2011

(65) Prior Publication Data

US 2011/0172261 A1 Jul. 14, 2011

Related U.S. Application Data

(60) Provisional application No. 61/294,911, filed on Jan. 14, 2010.

(51) Int. Cl.
*A61K 31/473* (2006.01)
*C07D 221/18* (2006.01)

(52) U.S. Cl.
USPC .......... 514/284; 546/78

(58) Field of Classification Search
USPC .......... 514/284; 546/78
See application file for complete search history.

(56) References Cited

U.S. PATENT DOCUMENTS 7,332,502 B2 2/2008 Lee et al.

FOREIGN PATENT DOCUMENTS

WO 2007/081540 7/2007

OTHER PUBLICATIONS

Grande, M.T. et al.: Synthesis of 2- and 3-substituted-1,2,3,4-tetrahydrodibenzo[th]isoquinolines. J. Heterocyclic Chem., vol. 23, pp. 929-933, 1986.*

McIver, A. et al.: A general approach to triphenylenes and azatriphenylenes: total synthesis of dehydrotylophorine and tylophorine. Chem. Commun., pp. 4750-4752, 2008.*

Govindachari, T.R. et al.: Chemical examination of Tylophora Asthmatica-III. Tetrahedron, vol. 9, pp. 53=57, 1960.*

Wu et al., "Phenanthroindolizidine Alkaloids and Their Cytotoxicity from the Leaves of Ficus Septica", *Heterocycles*, vol. 57, No. 12, 2002, pp. 2401-2408.

Buckley III et al., "α-Amino Acids as Chiral Educts for Asymmetric Products. Chirally Specific Syntheses of Tylophorine and Cryptopleurine", *J. Org. Chem.* 1983, 48, 4222-4232.

Yang et al., "Novel Small-Molecule Inhibitors of Transmissible Gastroenteritis Virus", *Antimicrobial Agents and Chemotherapy*, Nov. 2007, vol. 51, No. 11, p. 3924-3931.

Barnard et al., "Enhancement of the infectivity of SARS-CoV in BALB/c mice by IMP dehydrogenase inhibitors, including ribavirin", *Antiviral Research*, 71 (2006) 53-63.

Cai et al., "Phenanthroquinolizidine Alkaloids from the Roots of *Boehmeria pannosa* Potently Inhibit Hypoxia-Inducible Factor-1 in AGS Human Gastric Cancer Cells", *J. Nat. Prod.* 2006, 69, 1095-1097.

Yang et al., "Anti-Inflammatory Mechanisms of Phenanthroindolizidine Alkaloids", *Mol Pharmacol*, 69:749-758, 2006.

Chuang et al., "Expedient synthesis and structure-activity relationships of phenanthroindolizidine and phenanthroquinolizidine alkaloids", *Org. Biomol. Chem.*, 2006, 4, 860-567.

Yang et al., "Anti-inflammatory effects of 7-methoxycryptopleurine and structure-activity relations of phenanthroindolizidines and phenanthroquinolizidines", *Biochemical and Biophysical Research Communications*, 354 (2007) 942-948.

Yang et al., "Anti-Inflammatory Mechanisms of Phenanthroindolizidine Alkaloids," Molecular Pharmacology, 69:749-758 (2006).

* cited by examiner

*Primary Examiner* — Charanjit Aulakh

(74) *Attorney, Agent, or Firm* — Occhiuti Rohlicek & Tsao LLP

(57) ABSTRACT

A group of novel dibenzo[f,h]isoquinoline derivatives as shown in the specification. Also disclosed are methods of using the compounds for treating a disease associated with NO overproduction, cancer, or viral infection.

26 Claims, No Drawings

DIBENZO[F,H]ISOQUINOLINE DERIVATIVES

CROSS-REFERENCE TO RELATED APPLICATION

Pursuant to 35 U.S.C. §119(e), this application claims the benefit of the priority of U.S. Provisional Patent Application No. 61/294,911, filed Jan. 14, 2010. The content of the prior application is incorporated herein by its entirety.

BACKGROUND

Nitric oxide (NO) is an important pleiotropic molecule mediating a wide range of physiological and pathophysiological processes. For example, it enhances activity of cyclooxygenase II (COX-II), an enzyme responsible for the synthesis of prostaglandins, which mediate inflammation, pain, and fever. See Liu, et al., Carcinogenesis, 2003, Vol. 24, No. 4, 637-642.

NO is produced from L-arginine and molecular oxygen by three distinct isoforms of nitric oxide synthase (NOS), i.e., neural NOS (nNOS), endothelial NOS (eNOS), and inducible NOS (iNOS). Among the three isoforms, iNOS can be induced by endotoxins, cytokines (e.g., TNF-α), and certain transcriptional factors (e.g., NF-κB and AP1). It is the major target for preventing NO overproduction.

SUMMARY

This invention is based on the discovery that a group of dibenzo[f,h]isoquinoline derivatives are effective in inhibiting NO production. These compounds are also found to have anticancer and antivirus activities.

One aspect of the present invention relates to the compounds of Formula I:

Formula I

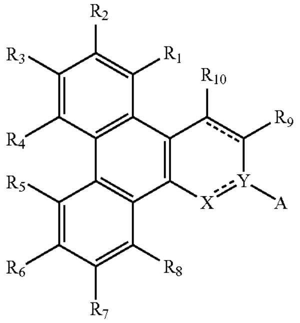

in which each of $R_1$, $R_2$, $R_3$, $R_4$, $R_5$, $R_6$, $R_7$, $R_8$, $R_9$, and $R_{10}$, independently, is H, alkyl, alkenyl, alkynyl, cycloalkyl, heterocycloalkyl, aryl, heteroaryl, halo, nitro, cyano, —$OR^a$, —$OC(O)R^a$, —$C(O)OR^a$, —$NR^aR^b$, —$NR^aC(O)R^b$, or —$C(O)NR^aR^b$, each of $R^a$ and $R^b$, independently, being H, alkyl, aryl, heteroaryl, cycloalkyl, or heterocycloalkyl; X══Y, together, are C(R')(R")—N or CR'═$N^+$, in which R' is H, alkyl, alkenyl, alkynyl, cycloalkyl, heterocycloalkyl, aryl, heteroaryl, halo, nitro, or cyano, and R" is H, alkyl, alkenyl, alkynyl, cycloalkyl, heterocycloalkyl, aryl, heteroaryl, halo, nitro, cyano, —$OR^c$, or —$OC(O)R^c$, $R^c$ being H, alkyl, aryl, heteroaryl, cycloalkyl, or heterocycloalkyl; ══ is a single bond or a double bond; and A is H, alkyl, alkenyl, alkynyl, cycloalkyl, heterocycloalkyl, aryl, or heteroaryl.

Referring to Formula I, a subset of the compounds described above feature that A is unsubstituted alkyl (e.g., A being $CH_2CH_3$, $(CH_2)_2CH_3$, or $CH(CH_3)_2$), or alkyl substituted with one or more groups selected from halo, alkenyl, alkynyl, aryl, heteroaryl, cycloalkyl, heterocycloalkyl, nitro, cyano, —$OR^d$, —$OC(O)R^d$, —$C(O)OR^d$, —$NR^dR^e$, —$NR^dC(O)R^e$, or —$C(O)NR^dR^e$, each of $R^d$ and $R^e$, independently, being H, alkyl, cycloalkyl, heterocycloalkyl, aryl, or heteroaryl (e.g., A being $C_{2-3}$ alkyl substituted with OH); $R_3$ is —$OR^a$, in which $R^a$ is H or alkyl; each of $R_6$ and $R_7$ is —$OR^a$, in which $R^a$ is H or alkyl; or R' is H and R" is H or OH.

Another subset of the compounds described above have the following formula:

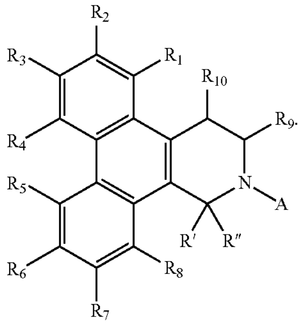

In this formula, A is unsubstituted alkyl (e.g., A being $CH_2CH_3$, $(CH_2)_2CH_3$, or $CH(CH_3)_2$), or alkyl substituted with one or more groups selected from halo, alkenyl, alkynyl, aryl, heteroaryl, cycloalkyl, heterocycloalkyl, nitro, cyano, —$OR^d$, —$OC(O)R^d$, —$C(O)OR^d$, —$NR^dR^e$, —$NR^dC(O)R^e$, or —$C(O)NR^dR^e$, each of $R^d$ and $R^e$, independently, being H, alkyl, cycloalkyl, heterocycloalkyl, aryl, or heteroaryl (e.g., A being $C_{2-3}$ alkyl substituted with OH); $R_3$ is —$OR^a$, in which $R^a$ is H or alkyl; each of $R_6$ and $R_7$ is —$OR^a$, in which $R^a$ is H or alkyl; or R' is H and R" is H or OH.

The present invention also relates to a method of suppressing NO production or treating a disease associated with NO overproduction (e.g., an inflammatory disease) by administering to a subject in need of the treatment an effective amount of a compound of Formula I. In one example, the subject suffers from arthritis or atherosclerosis.

The compounds of this invention have anticancer and antivirus activities. Thus, the present invention also relates to a method of treating cancer or viral infection by administering to a subject in need of the treatment an effective amount of a compound of Formula I.

Also within the scope of this invention is use of a compound of Formula I for treating any of the diseases mentioned above or for the manufacture of a medicament in the treatment.

The term "alkyl" refers to a straight or branched hydrocarbon, containing 1-10 carbon atoms. Examples of alkyl groups include, but are not limited to, methyl, ethyl, n-propyl, i-propyl, n-butyl, i-butyl, and t-butyl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cyclyl" refers to a saturated and partially unsaturated cyclic hydrocarbon group having 3 to 12 carbons, preferably 3 to 8 carbons, and more preferably 3 to 6 carbons, wherein the cyclyl group may be optionally substituted.

Examples of cyclyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein each ring may have 1 to 4 substituents. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

Alkyl, aryl, cyclyl, heteroaryl, and heterocyclyl mentioned herein include both substituted and unsubstituted moieties. Examples of a substituent include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl are optionally further substituted with alkyl, aryl, heteroaryl, halogen, hydroxyl, amino, mercapto, cyano, or nitro.

The compound of this invention may include an anion. The term "anion" refers to a negatively charged ion. Examples of an anion include, but are not limited to, $Cl^-$, $Br^-$, $I^-$, $SO_4^{2-}$, $PO_4^{3-}$, $ClO_4^-$, $CH_3CO_2^-$, and $CF_3CO_2^-$.

Shown in the table below are exemplary compounds of this invention:

| Structure | R | Compound No. |
| --- | --- | --- |
| 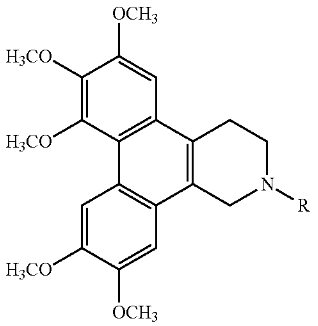 | $-CH_2CH_3$<br>$-(CH_2)_2CH_3$<br>$-(CH_2)_3CH_3$<br>$-CH(CH_3)_2$ | 1<br>2<br>3<br>4 |
| 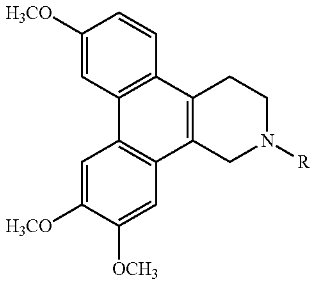 | $-CH_2CH_3$<br>$-(CH_2)_2CH_3$<br>$-(CH_2)_3CH_3$ | 5<br>6<br>7 |
| 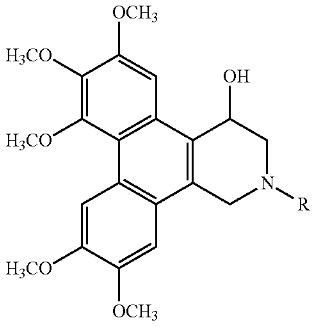 | $-(CH_2)_2CH_3$ | 8 |

-continued

| Structure | R | Compound No. |
| --- | --- | --- |
| 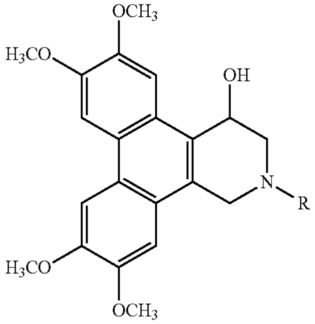 | $—CH_2CH_3$<br>$—(CH_2)_2CH_3$<br>$—(CH_2)_3CH_3$<br>$—CH_2CH(CH_3)_2$<br>$—(CH_2)_4CH_3$<br>$—CH(CH_3)_2$<br>$—CH(CH_3)CH_2CH_3$<br>$—(CH_2)_3OTHP$<br>$—(CH_2)_3OH$ | 9<br>10<br>11<br>12<br>13<br>14<br>15<br>16<br>17 |
| 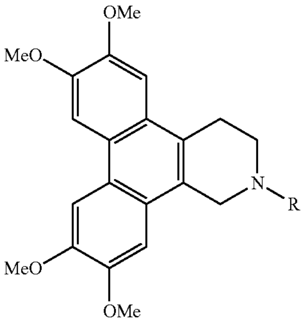 | $—CH_2CH_3$<br>$—(CH_2)_2CH_3$<br>$—(CH_2)_3CH_3$<br>$—CH_2CH(CH_3)_2$<br>$—(CH_2)_4CH_3$<br>-2-methyl-[1,3]dioxolane<br>-2-ethyl-[1,3]dioxolane<br>$—CH(CH_3)_2$<br>$—CH(CH_3)CH_2CH_3$<br>$—(CH_2)_3OTHP$<br>$—(CH_2)_3OH$ | 18<br>19<br>20<br>21<br>22<br>23<br>24<br>25<br>26<br>27<br>28 |
| 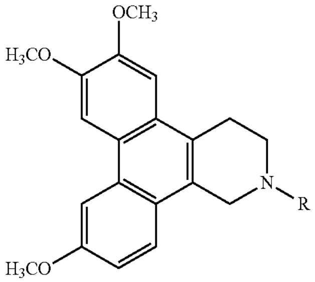 | $—(CH_2)_2CH_3$ | 29 |
| 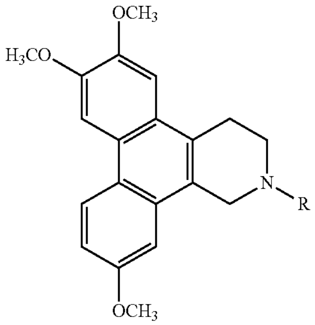 | $—CH_2CH_3$<br>$—(CH_2)_2CH_3$ | 30<br>31 |
| 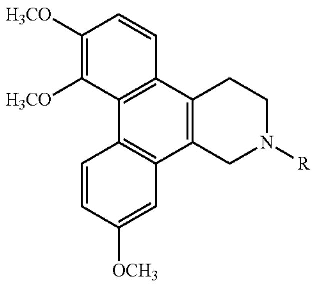 | $—(CH_2)_2CH_3$ | 32 |

-continued

| Structure | R | Compound No. |
| --- | --- | --- |
| 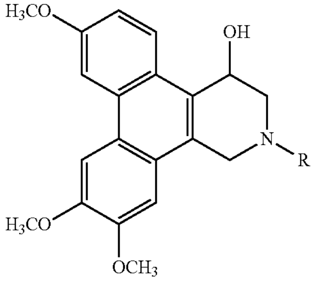 | —$CH_2CH_3$ | 33 |
| 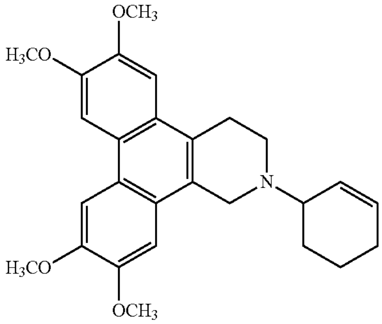 [SMILES: COc1cc2c3c(c4cc(OC)c(OC)cc4c2cc1OC)CN(C1C=CCCC1)CC3] | | 34 |
| 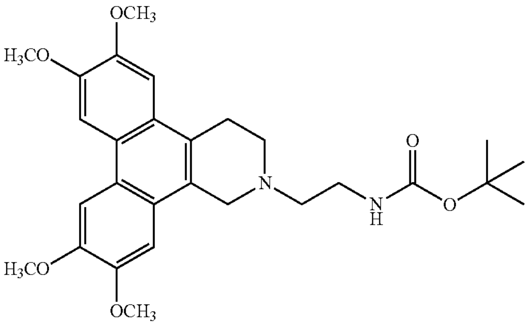 [SMILES: COc1cc2c3c(c4cc(OC)c(OC)cc4c2cc1OC)CN(CCNC(=O)OC(C)(C)C)CC3] | | 35 |
| 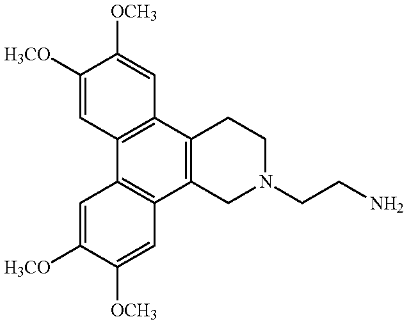 [SMILES: COc1cc2c3c(c4cc(OC)c(OC)cc4c2cc1OC)CN(CCN)CC3] | | 36 |

The details of many embodiments of the invention are set forth in the description below. Other features, objects, and advantages of the invention will be apparent from the description and the claims.

DETAILED DESCRIPTION

The compounds of this invention can be synthesized by conventional methods. For example, one can first prepare phenanthrene-9-carbaldehyde via the conventional synthetic route depicted in Scheme 1 below:

Scheme 1
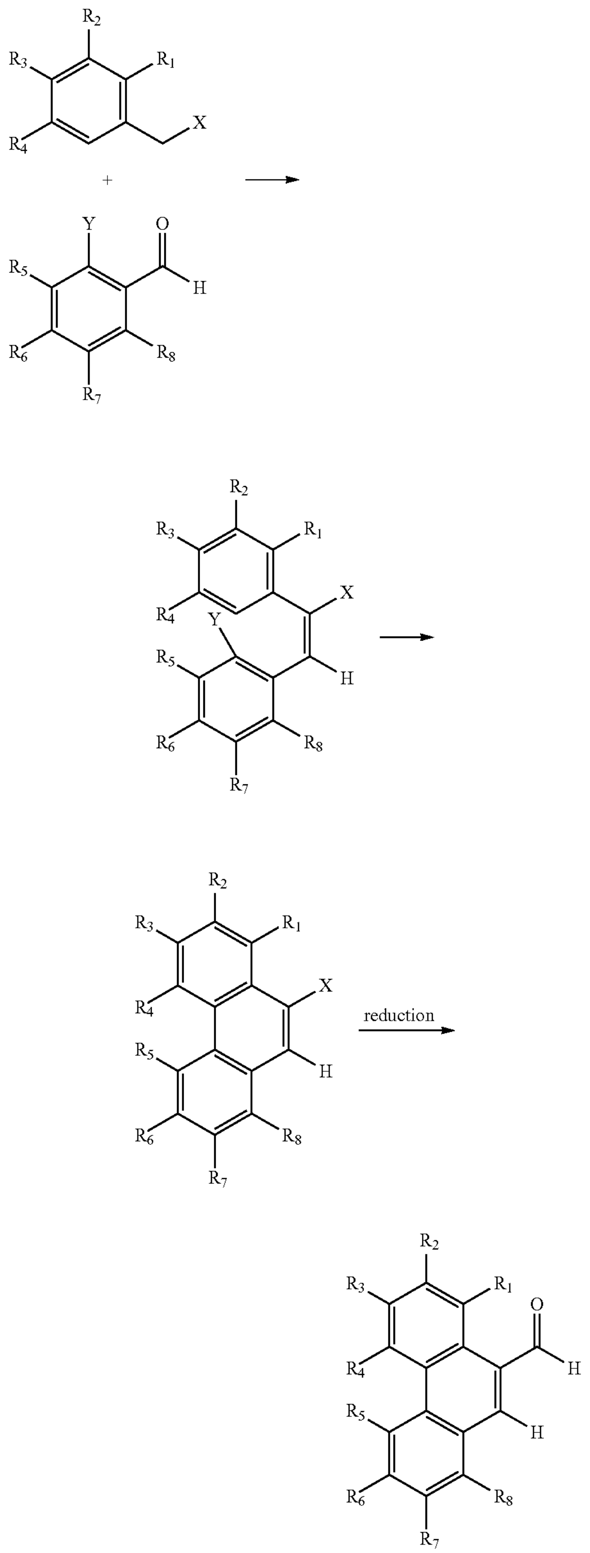
X is COOH, COO-alkyl, or CN
Y is H or $NO_2$
One can further conduct the reactions shown in Scheme 2 below to obtain compounds of formula I.
Scheme 2
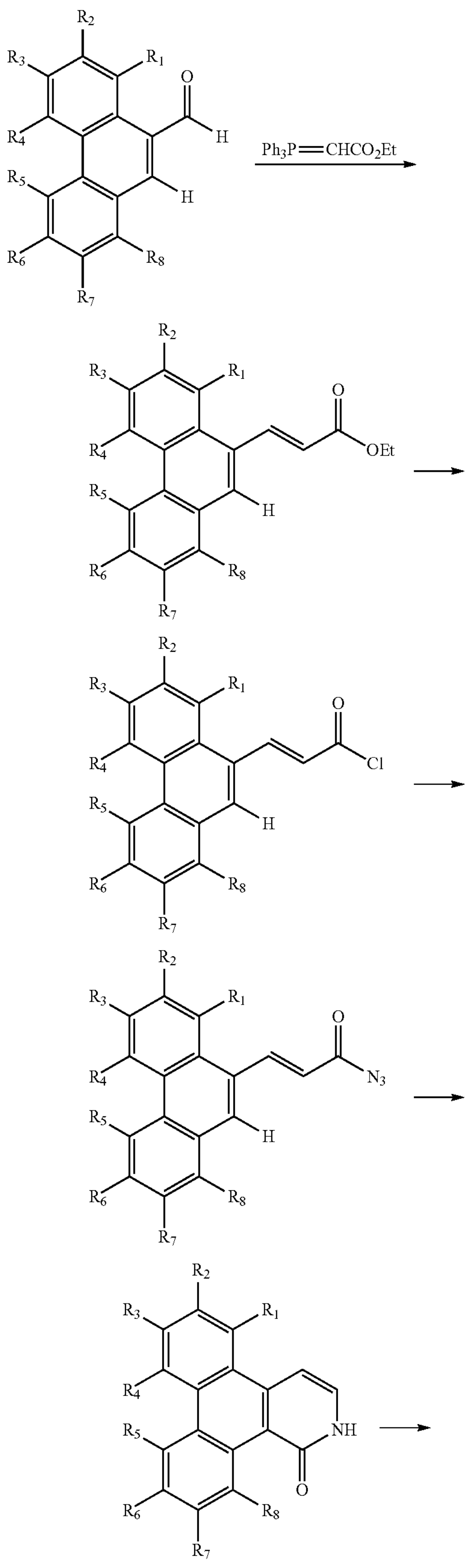

-continued

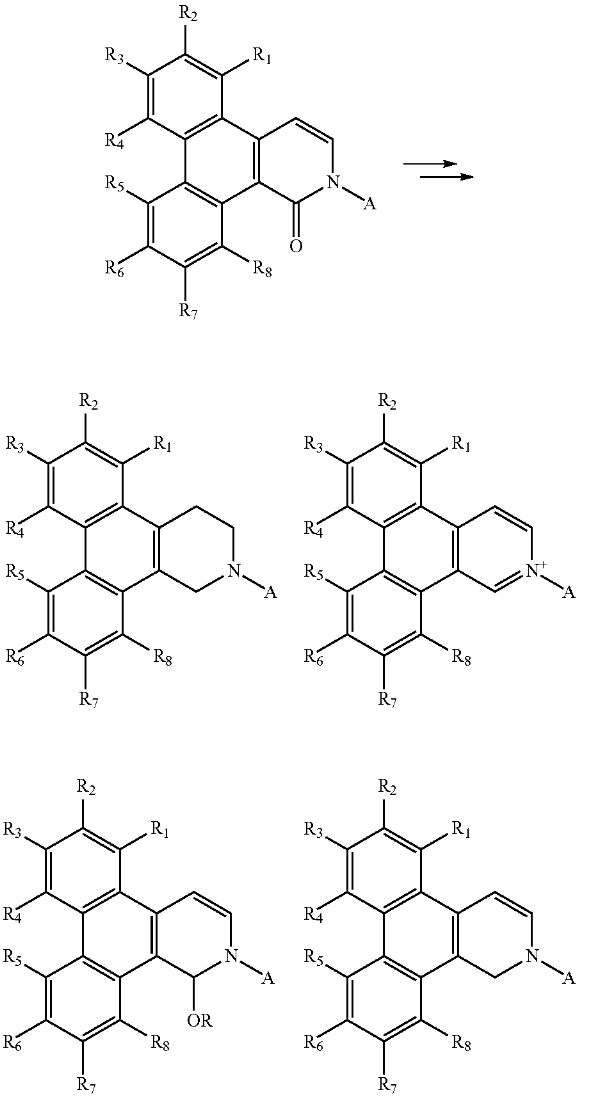

More specifically, the phenanthrene-9-carbaldehyde thus obtained is converted into (E)-ethyl 3-(phenanthren-9-yl) acrylate by the Wittig reaction. The resultant ester is then converted to an acyl azide compound via several steps, followed by the Curtis rearrangement reaction to form an additional six-membered N-containing ring. Alkylation at the N atom results in compounds in which N is substituted with alkyl, alkenyl, alkynyl, cycloalkyl, heterocycloalkyl, aryl, or heteroaryl. Reduction of these compounds affords compounds of this invention.

The reactions described above are all well known in the art. One would understand solvents, reagents, catalysts, and protecting group and deprotecting group reagents necessary for conducting these reactions. Synthetic chemistry transformations and protecting group methodologies (protection and deprotection) useful in synthesizing applicable dibenzo[f,h] isoquinoline compounds include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The compounds mentioned above may contain one or more asymmetric centers. Thus, they occur as racemates and racemic mixtures, single enantiomers, individual diastereomers, diastereomeric mixtures, or cis- or trans-isomeric forms. All such isomeric forms are contemplated.

When used for treating a disease associated with NO overproduction, cancer, or viral infection, an effective amount of any of the compounds described herein is administered to a subject in need of the treatment via a conventional route. The term "treating" refers to administering the compound to a subject who has a disorder, (i.e., cancer or a disease associated with NO overproduction), or has a symptom of the disorder, or has a predisposition toward the disorder, with the purpose to cure, heal, alleviate, relieve, alter, remedy, ameliorate, improve, or affect the disorder, the symptoms of the disorder, or the predisposition toward the disorder. The term "an effective amount" refers to the amount of the compound that is required to confer one of the above-described effects on the subject. The effective amount varies, as recognized by those skilled in the art, depending on the types of the effects, route of administration, excipient usage, and the possibility of co-usage with other treatment.

Diseases associated with NO overproduction include inflammatory diseases. An inflammatory disease is characterized by a local or systemic, acute or chronic inflammation. Examples of an inflammatory diseases include systemic lupus erythematosus, encephalitis, meningitis, arthritis, atherosclerosis, hepatitis, sepsis, sarcoidosis, psoriasis, Type I diabetes conjunctivitis, asthma, arteriosclerosis, chronic obstructive pulmonary disease, sinusitis, dermatitis, inflammatory bowel disease, ulcerative colitis, Crohn's disease, Behcet's syndrome, and graft rejection.

Cancer refers to a disease involving abnormal cell proliferation, cell invasion or metastasis, irrespective of the histopathologic nature of the proliferated cells or stage of invasiveness. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, and cancer of unknown primary site.

Viral infection can be caused by coronavirus, e.g., human CoV 229E, transmissible gastroenteritis virus (TGEV), mouse hepatitis virus, bovine CoV, infectious bronchitis virus, Feline coronaviruses (FCoV), or a SARS-associated CoV (SARS CoV).

To practice the methods of the present invention, a composition having one or more of the above-described compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active dibenzo[f,h]isoquinoline compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow # 10.

The effects of a compound can be tested by an in vitro or in vivo assay. For example, compounds of Formula I can be preliminarily screened by in vitro assays in which the compounds are tested for their efficacy in inhibiting cancer cell growth. Compounds that demonstrate high efficacy in the preliminary screening can be further evaluated by in vivo methods well known in the art to evaluate their activity in treating cancer.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of Compounds

Compound 1 was synthesized by the methods illustrated in the following scheme.

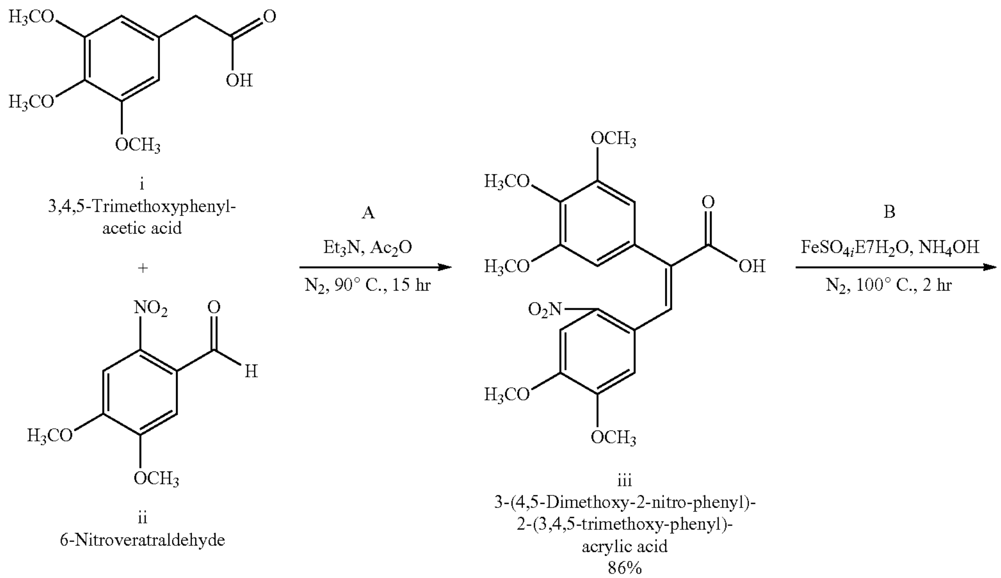

i
3,4,5-Trimethoxyphenyl-acetic acid
+
ii
6-Nitroveratraldehyde iii
3-(4,5-Dimethoxy-2-nitro-phenyl)-2-(3,4,5-trimethoxy-phenyl)-acrylic acid
86%

-continued

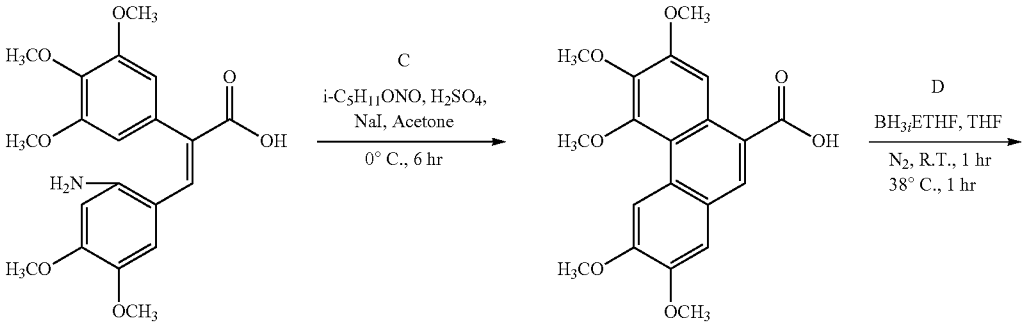

iv
3-(2-Amino-4,5-dimethoxy-phenyl)-2-(3,4,5-trimethoxy-phenyl)-acrylic acid
87% v
2,3,5,6,7-Pentamethoxy-phenanthrene-9-carboxylic acid
72%

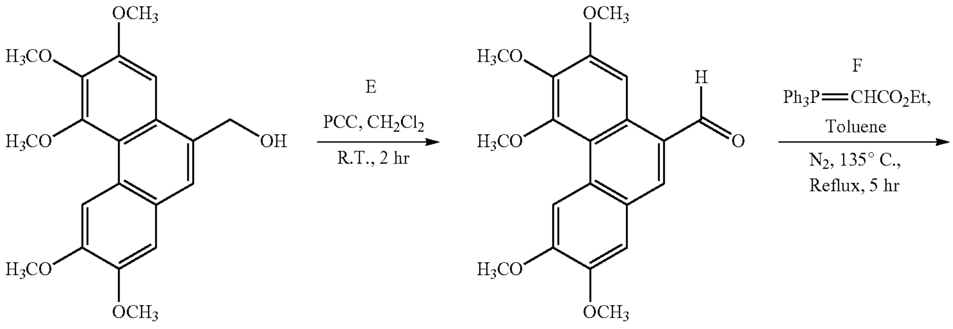

vi
2,3,5,6,7-Pentamethoxy-9-(hydroxymethyl)phenanthrene
97% vii
2,3,5,6,7-Pentamethoxy-phenanthrene-9-carbaldehyde
85%

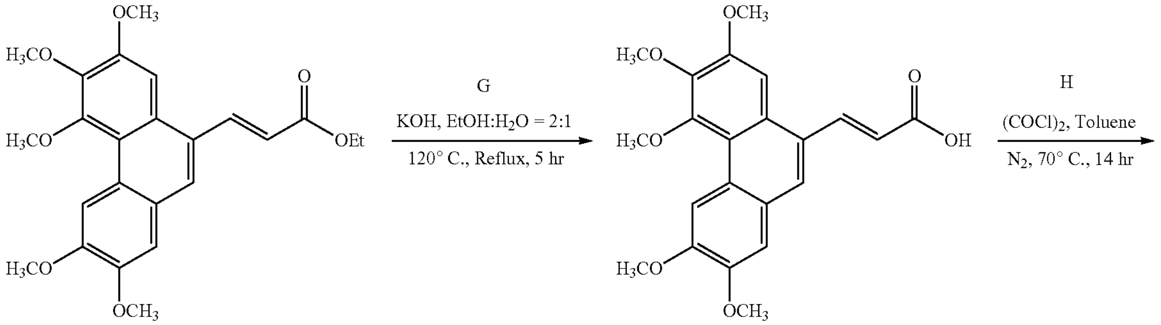

viii
3-(2,3,5,6,7-Pentamethoxy-phenanthren-9-yl)acrylic acid ethyl ester
99% ix
3-(2,3,5,6,7-Pentamethoxy-phenanthrene-9-yl)-acrylic acid
97%

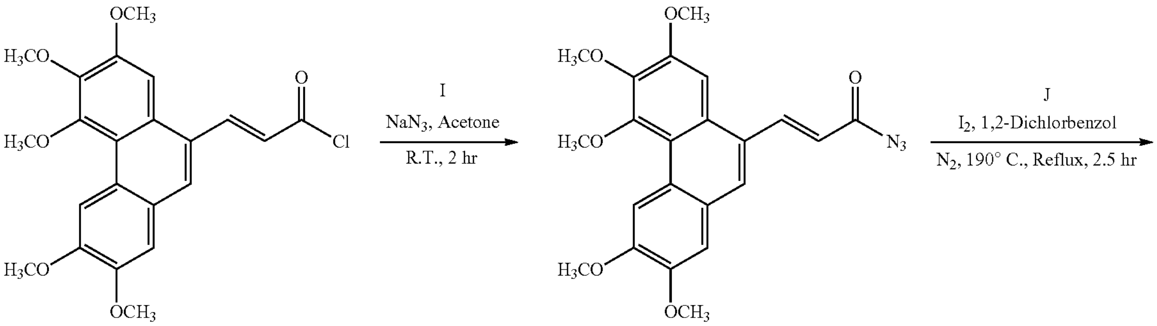

3-(2,3,5,6,7-Pentamethoxy-phenanthern-9-yl)-acryloyl chloride 3-(2,3,5,6,7-Pentamethoxy-phenanthrene-9-yl)-acryloyl azide -continued

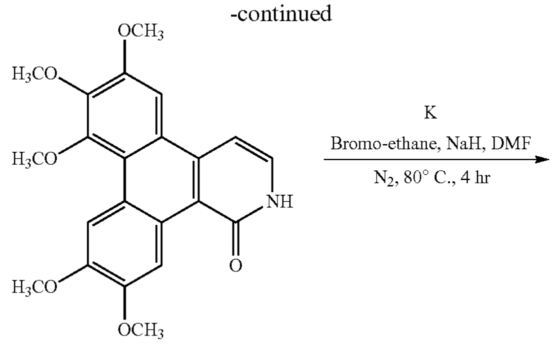

x
6,7,8,10,11-Pentamethoxy-2H-2-Aza-triphenylen-1-one
three step 66%

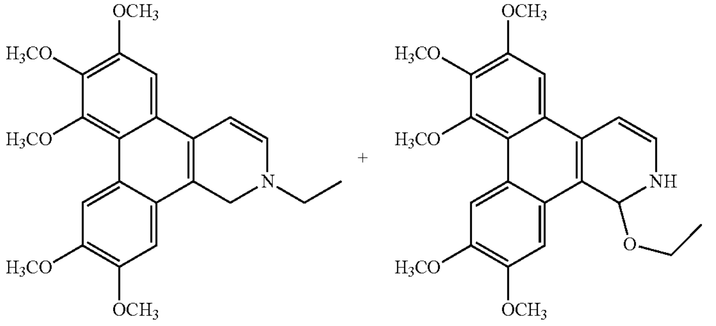

xi
6,7,8,10,11-Pentamethoxy-2-propyl-2H-2-aza-triphenylene-1-one
76%

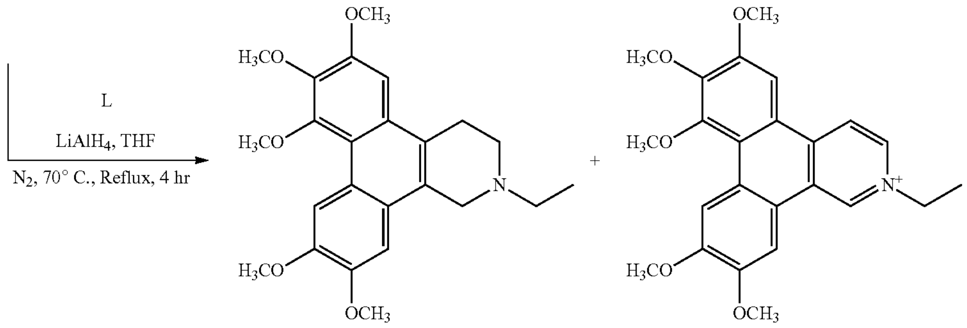

Compound 1
6,7,8,10,11-Pentamethoxy-2-propyl-1,2,3,4-tetrahydro-2-aza-triphenylene
23.3%

6,7,8,10,11-Pentamethoxy-2-propyl-2-azonia-triphenylene
9.4%

Compound i (10 mmol) and compound ii (10 mmol) were condensed in 10 mL acetic anhydride in the presence of $Et_3N$ (10 mmol) under $N_2$ at 90° C. for 15 hr. After extraction with $CH_2Cl_2$ and cryastallization in EtOAc, compound iii was obtained at the yield of 86%. Compound iii (9.5 mmol) was treated with $FeSO_4.7H_2O$ (95 mmol) in 97 mL $NH_4OH$ under $N_2$ at 100° C. for 2 hr, followed by addition of $H_3PO_4$ and extraction with $CHCl_3$:2-propanol (3:1), to afford compound iv at the yield of 87%. Compound iv (5.8 mmol) was reacted with isoamyl nitrite (11.6 mmol) in the presence of $H_2SO_4$ (11.6 mmol), NaI (58 mmol) and Acetone 330 mL to form phenanthrene-9-carboxylic acid compound v, which was purified by extraction with $CH_2Cl_2$ and washing with EtOAc to give the pure compound at a yield of 72%.

Compound v (2.6 mmol) was then reduced by $BH_3$.THF (7.8 mmol) in 32 mL THF to give phenanthrene-9-hydroxymethane compound vi at 97%, after purification by extraction. Compound vi (4.3 mmol) was then oxidized by PCC (6.4 mmol) in 29 mL $CH_2Cl_2$ to form aldehyde compound vii, which was passed through a silica gel column using $CH_2Cl_2$ as the eluent to give the pure compound (yield: 85%). Compound vii (6.3 mmol) was then refluxed with $Ph_3P{=}CHCO_2Et$ (8.8 mmol) in 65 mL toluene under $N_2$ at 135° C. for 5 hr to give compound viii at a yield of 99% after purification by a silica gel column. Compound viii was then hydrolyzed in 84 mL EtOH/$H_2O$ (2:1) containing KOH (15.8 mmol). The resulting solution was neutralized with HCl. The precipitate was filtered out and washed with MeOH to give compound ix (97%). Compound ix (0.25 mmol) was reacted with $(COCl)_2$ (0.5 mmol) in 4 mL toluene at 70° C. for 14 hr to produce an acyl chloride compound, which was used without further purification to react with $NaN_3$ (0.75 mmol) in 12 mL acetone for 2 hr at room temperature. The crude product was purified by silica gel chromatography. The purified compound was suspended in 2.5 mL dichlorobenzene and a piece of $I_2$ was added. The reaction mixture was heated at 190° C. for 2.5 hr to give compound x, after silica gel purification. The overall yield over the last three steps was 66%. Compound xii (0.25 mmol) was reacted with bromoethane (1.25 mmol) and NaH (0.63 mmol) in 2 mL THF at 80° C. for 4 hr. The crude product was purified by give pure compound xi at a yield of 76%. Compound xi (0.37 mmol) was reacted with $LiAlH_4$ (1.85 mmol) in 10 mL THF at 70° C. for 4 hr. After a gradient silica gel chromatography using $CHCl_3$/n-Hexane 5:1 to 2:1, Compound 1 and compound xii were obtained at yields of 23.3% and 9.4%, respectively.

Compounds 2-7 were synthesized in the manner similar to that described above.

Alternatively, compound 8 was synthesized via the following synthetic route:

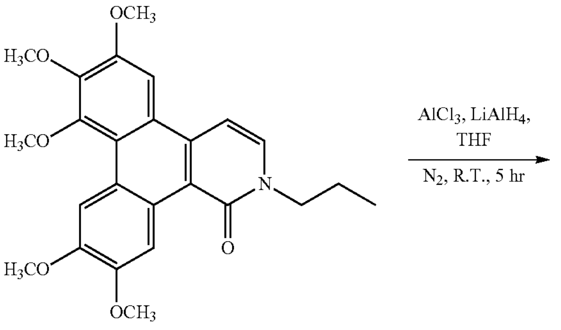

xii

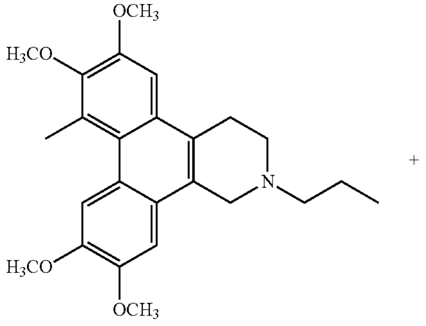

Compound 2

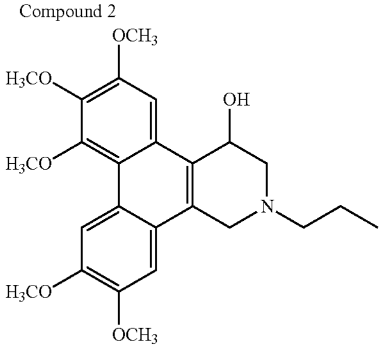

Compound 8

As shown above, compound xii (0.19 mmol) was reacted with $AlCl_3$ (0.59 mmol) and $LiAlH_4$ (2.09 mmol) in 2 mL THF at room temperature for 5 hr. The crude product was purified by HPLC eluted with $CH_2Cl_2$/EtOAc/MeOH (65:32:3) to give compound 2 (17%) and compound 5 (19.7%).

Compounds 9-28 were prepared by the methods shown in the following scheme:

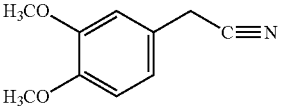

xiii

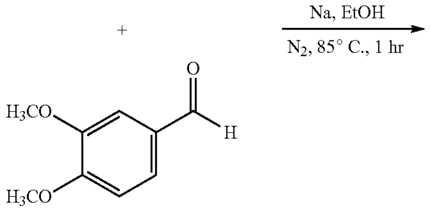

xiv

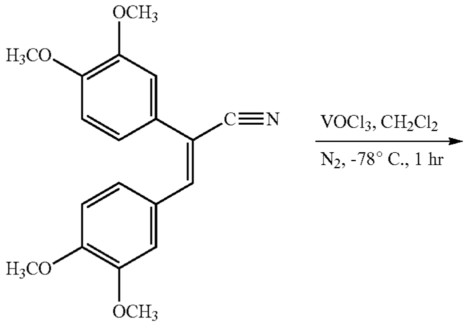

xv

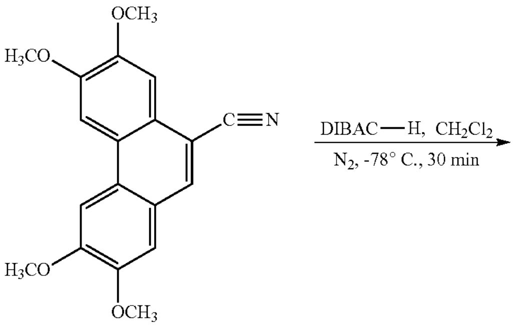

xvi

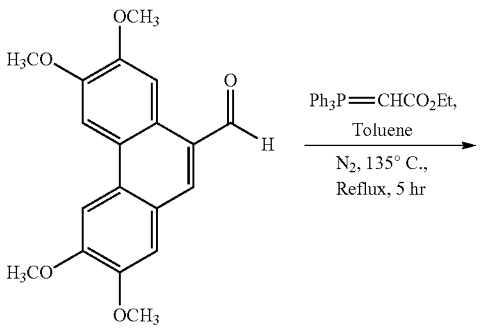

xvii

-continued
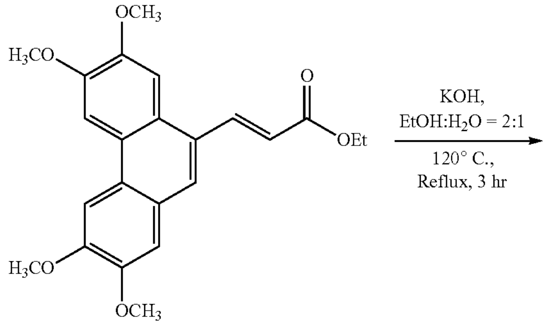
xviii
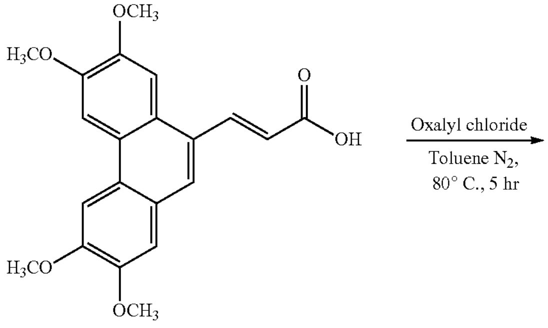
xix
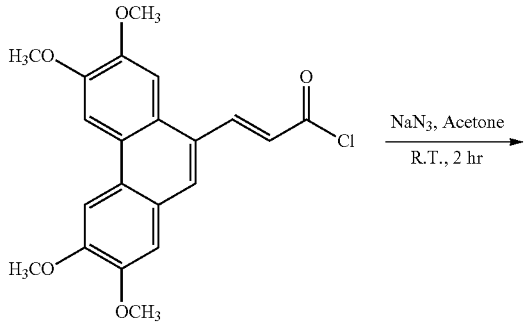
xx
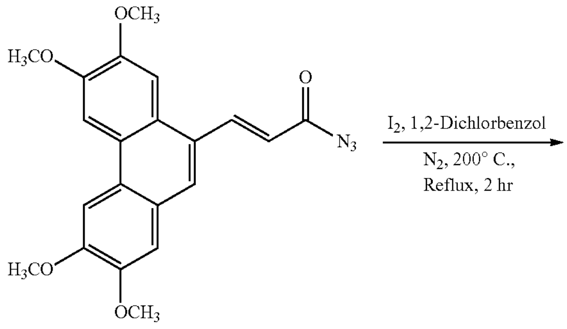
xxi
-continued
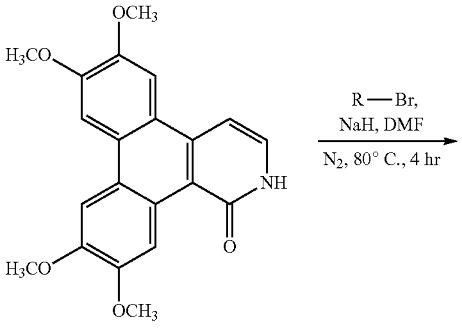
xxii
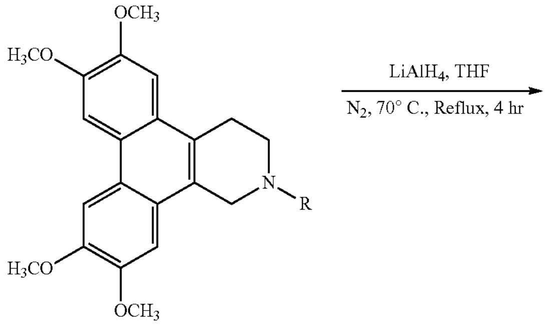
xxiii
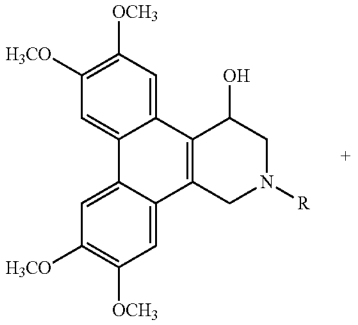
Compounds 9-17
R = —$CH_2CH_3$,
—$(CH_2)_2CH_3$,
—$(CH_2)_3CH_3$,
—$CH_2CH(CH_3)_2$
—$(CH_2)_4CH_3$,
—$CH(CH_3)_2$,
—$CH(CH_3)CH_2CH_3$,
—$(CH_2)_3OTHP$,
—$(CH_2)_3OH$ -continued

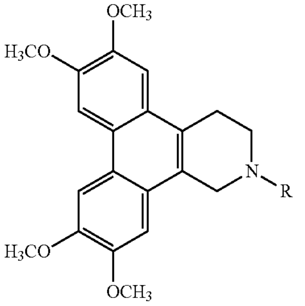

+

Compounds 18-28

R = —$CH_2CH_3$,
—$(CH_2)_2CH_3$,
—$(CH_2)_3CH_3$,
—$CH_2CH(CH_3)_2$
—$(CH_2)_4CH_3$,
-2-methyl-[1,3]dioxolane,
-2-ethyl-[1,3]dioxolane,
—$CH(CH_3)_2$,
—$CH(CH_3)CH_2CH_3$,
—$(CH_2)_3$OTHP,
—$(CH_2)_3$OH

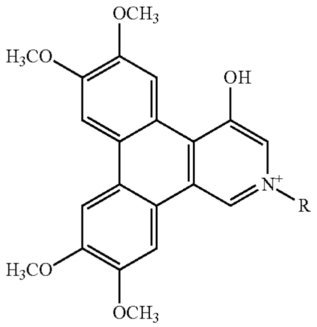

R = —$CH_2CH_3$,
—$(CH_2)_3CH_3$,
—$(CH_2)_4CH_3$,
—$CH(CH_3)_2$,
—$CH(CH_3)CH_2CH_3$,
—$(CH_2)_3$OTHP,
—$(CH_2)_3$OH $VOCl_3$: Vanadium oxytrichloride
DIBAC—H: Diisobutylaluminumhydride
$Ph_3P{=}CHCO_2Et$: Ethyl (Triphenylphosphoranylidene) acetate
$Bu_3SnH$: Tri-n-Butyltin hydride
AIBN: 2,2-Azobisisobutyronitrile)
NaAl $(OCH_2CH_2OMe)_2H_2$: Sodium bis (2-methoxyethoxy) aluminum hydride As shown above, compounds xiii and xiv were condensed to afford acrylonitrile compound xv, which was cyclized to give 9-cyanophenanthrene compound xvi. The cyano group of compound xvi was reduced to aldehyde to provide compound xvii, which was subjected to the Wittig reaction, hydrolysis, and acyl chlorination to produce acyl chloride xx. Compound xx was reacted with sodium azide to give acyl azide xxi, which underwent arrangement cyclization to provide compound xxii. Compound xxii was coupled with various bromoalkyl compounds and then reduced with $LiAlH_4$ to afford Compounds 9-28 and other compounds of formula I shown above.

Compound 29 was synthesized by the methods shown in the following scheme:

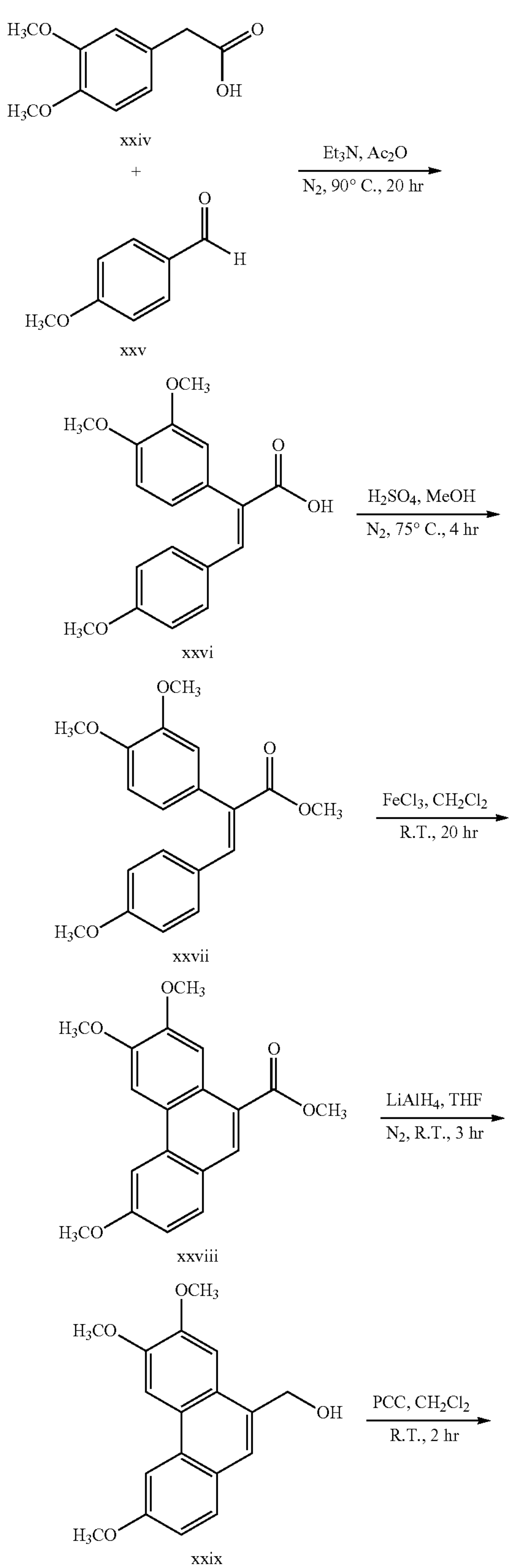 [SMILES: COc1ccc(CC(=O)O)cc1OC ; COc1ccc(C=O)cc1 ; COc1ccc(/C=C(/C(=O)O)c2ccc(OC)c(OC)c2)cc1 ; COC(=O)/C(=C/c1ccc(OC)cc1)c1ccc(OC)c(OC)c1 ; COC(=O)c1cc2ccc(OC)cc2c2cc(OC)c(OC)cc12 ; COc1ccc2cc(CO)c3cc(OC)c(OC)cc3c2c1]

-continued

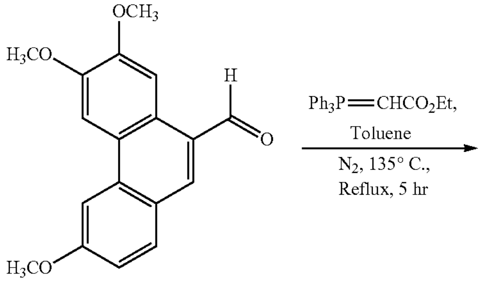

xxx

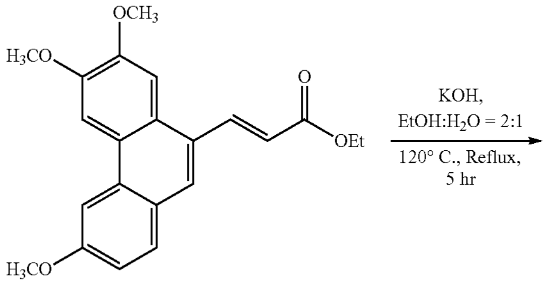

xxxi

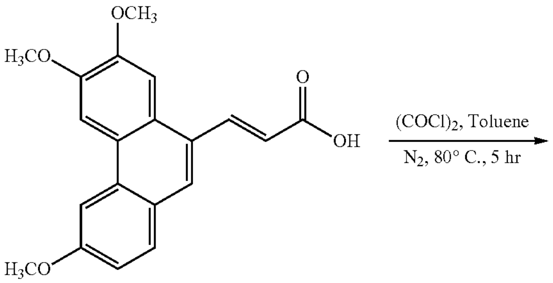

xxxii

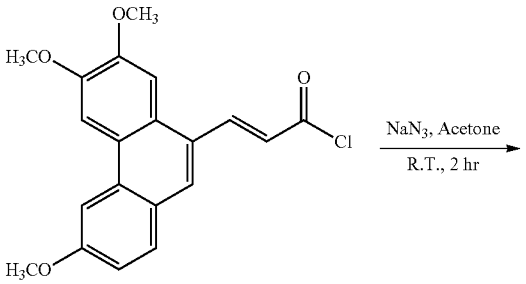

xxxiii

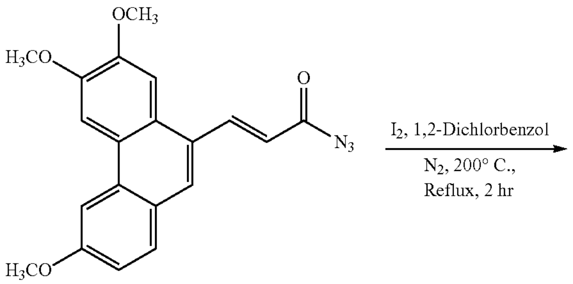

xxxiv

-continued

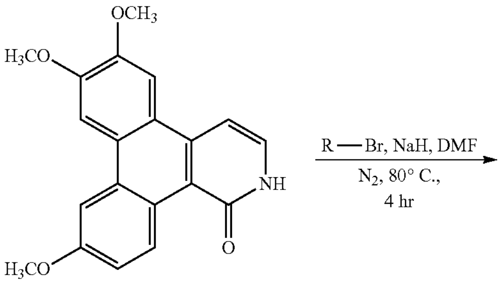

xxxv

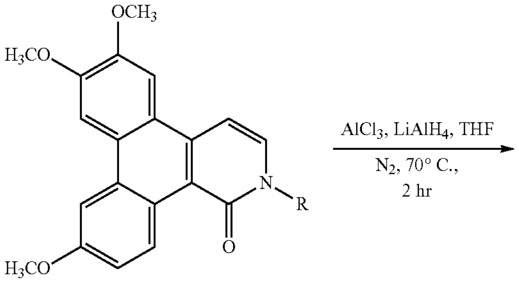

xxxvi

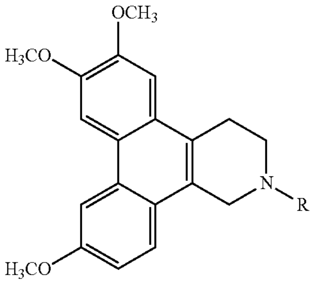

R = —$(CH_2)_2CH_3$,

Compound 29

$i-C_5H_{11}ONO$: Isoamyl nitrite
PCC: Pyridinium chlorochromate
$(COCl)_2$: Oxalyl chloride
$Ph_3P{=}CHCO_2Et$: Ethyl (Triphenylphosphoranylidene) acetate Compounds xxiv and xxv were condensed to afford compound xxvi, which was converted to an ester compound xxvii. Compound xxvii was cyclized to give 9-carboxyphenanthrene compound xxviii. The carboxy group of compound xxviii was reduced to hydroxyl and then oxidized to aldehyde to provide compound xxx, which was subjected to Wittig reaction, hydrolysis, and acyl chlorination to produce acyl chloride xxxii. Compound xxxii was reacted with sodium azide to give acyl azide xxxiv, which underwent arrangement to provide compound xxxv. Compound xxxv was coupled with various bromoalkyl compounds and then reduced with $LiAlH_4$ in the presence of $AlCl_3$ to afford compound 29.

Compounds 30-36 were synthesized in a manner similar to that described above.

Characterization data for some of the compounds prepared above are provided as follows.

Compound 1:

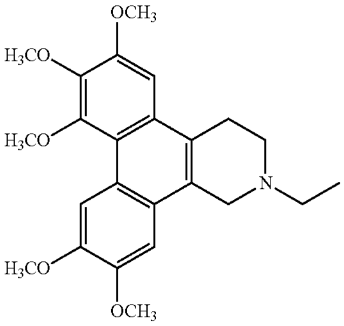

$^1$H-NMR (400 MHz, $CDCl_3$): 1.31 (3H, t, J=7.2 Hz), 2.79 (2H, q, J=7.2 Hz), 2.93 (2H, t, J=5.6 Hz), 3.19 (2H, t, J=5.6 Hz), 3.98 (3H, s), 4.01 (2H, s), 4.02 (3H, s), 4.04 (3H, s), 4.05 (3H, s), 4.09 (3H, s), 7.16 (1H, s), 7.18 (1H, s), 9.20 (1H, s).

Compound 2:

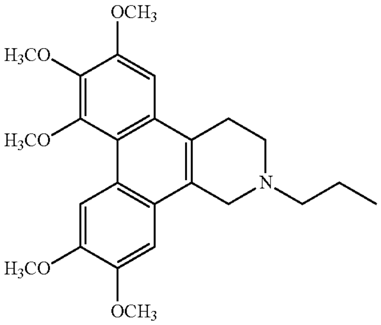

$^1$H-NMR (300 MHz, $CDCl_3$): 1.03 (3H, t, J=7.5 Hz), 1.74 (2H, sextet, J=7.5 Hz), 2.67 (2H, t, J=7.5 Hz), 2.92 (2H, t, J=6.0 Hz), 3.18 (2H, t, J=6.0 Hz), 3.98 (3H, s), 4.00 (2H, s), 4.02 (3H, s), 4.04 (3H, s), 4.05 (3H, s), 4.09 (3H, s), 7.16 (1H, s), 7.18 (1H, s), 9.19 (1H, s).

Compound 3:

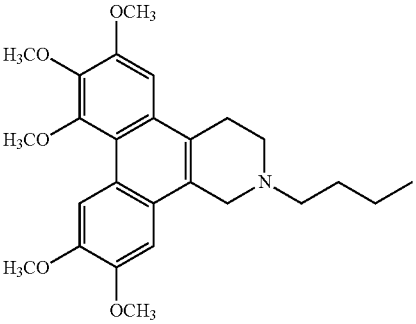

$^1$H-NMR (400 MHz, $CDCl_3$): 1.00 (3H, t, J=7.6 Hz), 1.45 (2H, sextet, J=7.6 Hz), 1.70 (2H, quintet, J=7.6 Hz), 2.71 (2H, t, J=7.6 Hz), 2.92 (2H, t, J=5.6 Hz), 3.18 (2H, t, J=5.6 Hz), 3.98 (3H, s), 4.00 (2H, s), 4.02 (3H, s), 4.05 (3H, s), 4.06 (3H, s), 4.09 (3H, s), 7.16 (1H, s), 7.18 (1H, s), 9.19 (1H, s).

Compound 4:

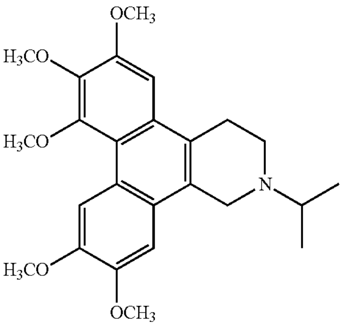

Light yellow crystal; mp 195~198° C.; MS (ES, positive mode): m/z 426 $(M+H)^+$; $^1$H NMR (300 MHz, $CDCl_3$): 1.12 (d, J=6.3 Hz, 6H), 2.97 (t, J=5.4 Hz, 2H), 3.11 (septet, J=6.3 Hz, 1H), 3.18 (t, J=5.4 Hz, 2H), 3.98 (s, 3H), 4.02 (s, 3H), 4.04 (s, 3H), 4.06 (s, 3H), 4.09 (s, 3H), 4.11 (s, 2H), 7.16 (s, 1H), 7.18 (s, 1H), 9.19 (s, 1H).

Compound 5:

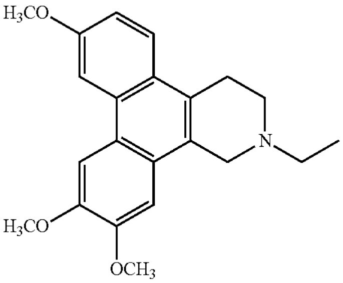

Yellow crystal; mp 160~161° C.; MS (ES, positive mode): m/z 352 $(M+H)^+$; $^1$H NMR (300 MHz, $CDCl_3$): 1.32 (t, J=7.2 Hz, 3H), 2.80 (q, J=7.2 Hz, 2H), 2.94 (t, J=5.7 Hz, 2H), 3.25 (t, J=5.7 Hz, 2H), 4.00 (s, 2H), 4.01 (s, 3H), 4.05 (s, 3H), 4.10 (s, 3H), 7.14 (s, 1H), 7.21 (dd, J=9.0, 2.6 Hz, 1H), 7.89 (d, J=2.6 Hz, 1H), 7.90 (s, 1H), 7.92 (d, J=9.0 Hz, 1H).

Compound 6:

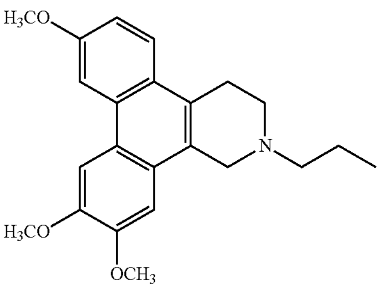

$^1$H-NMR (400 MHz, $CDCl_3$): 1.03 (3H, t, J=7.6 Hz), 1.75 (2H, sextet, J=7.6 Hz), 2.67 (2H, t, J=7.6 Hz), 2.92 (2H, t, J=6.0 Hz), 3.24 (2H, t, J=6.0 Hz), 3.98 (2H, s), 4.02 (3H, s), 4.05 (3H, s), 4.11 (3H, s), 7.15 (1H, s), 7.21 (1H, dd, J=9.2 Hz, J=2.4 Hz), 7.89 (1H, d, J=2.4 Hz), 7.92 (1H, s), 7.93 (1H, d, J=9.2 Hz).

Compound 7:

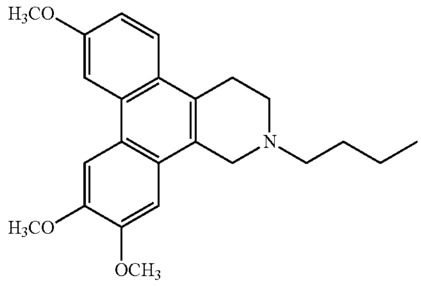

Yellow crystal; mp 130~131° C.; MS (APCI, positive mode): m/z 380 $(M+H)^+$; $^1$H NMR (300 MHz, $CDCl_3$): 1.00 (t, J=7.5 Hz, 3H), 1.45 (sextet, J=7.5 Hz, 2H), 1.71 (quintet, J=7.5 Hz, 2H), 2.71 (t, J=7.5 Hz, 2H), 2.92 (t, J=5.7 Hz, 2H), 3.23 (t, J=5.7 Hz, 2H), 3.98 (s, 2H), 4.02 (s, 3H), 4.05 (s, 3H), 4.11 (s, 3H), 7.12 (s, 1H), 7.21 (dd, J=9.0, 2.6 Hz, 1H), 7.88 (d, J=2.6 Hz, 1H), 7.90 (s, 1H), 7.92 (d, J=9.0 Hz, 1H).

Compound 8:

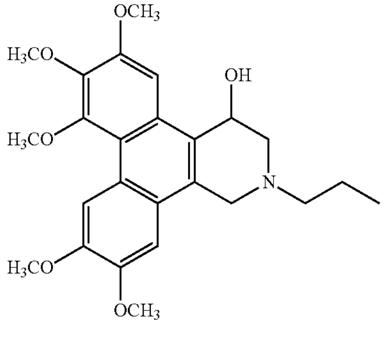

Light yellow crystal; mp 213~214° C.; MS (ES, positive mode): m/z 442 $(M+H)^+$; $^1$H NMR (600 MHz, $CDCl_3$): 1.01 (t, J=7.8 Hz, 3H), 1.72 (sextet, J=7.8 Hz, 2H), 2.54 (dd, J=11.1, 2.1 Hz, 1H), 2.59 (ddt, J=15.3, 12, 7.8 Hz, 1H), 2.68 (ddt, J=15.3, 12, 7.8 Hz, 1H), 3.35 (d, J=11.1 Hz, 1H), 3.47 (d, J=15.3 Hz, 1H), 3.97 (s, 3H), 4.00 (s, 3H), 4.05 (s, 3H), 4.06 (s, 3H), 4.09 (s, 3H), 4.11 (d, J=15.3 Hz, 1H), 5.09 (s, 1H), 6.96 (s, 1H), 7.64 (s, 1H), 9.16 (s, 1H). $^{13}$C NMR (150 MHz, $CDCl_3$): 11.9, 20.0, 54.4, 55.6, 55.7, 55.8, 57.9, 60.1, 60.5, 61.3, 64.9, 101.4, 102.5, 107.8, 118.2, 123.9, 124.4, 127.7, 128.1, 128.3.

Compound 9:

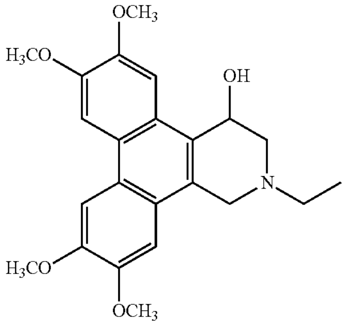

White needle; mp 185° C.; MS (ES, positive mode): m/z 398 $(M+H)^+$; $^1$H NMR (300 MHz, $CDCl_3$): 1.25 (t, J=7.2 Hz, 3H), 2.26 (d, J=11.1 Hz, 1H), 2.53 (m, 1H), 2.74 (m, 1H), 3.00 (d, J=15.6 Hz, 1H), 3.30 (m, 1H), 3.35 (d, J=11.1 Hz, 1H), 3.84 (s, 3H), 4.07 (s, 3H), 4.09 (s, 3H), 4.12 (s, 3H), 4.91 (s, 1H), 6.25 (s, 1H), 7.40 (s, 1H), 7.55 (s, 1H), 7.79 (s, 1H). $^{13}$C NMR (100 MHz, $CDCl_3$): 11.3, 52.2, 53.3, 55.6, 55.7, 55.8, 57.2, 64.6, 102.5, 102.5, 102.6, 105.1, 122.6, 123.6, 123.9, 125.3, 126.4, 126.6, 147.9, 148.2, 148.4, 148.5.

Compound 10

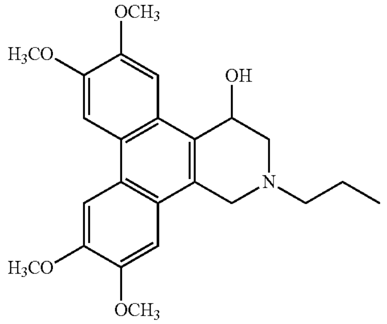

White rock; mp 202° C.; MS (ES, positive mode): m/z 412 $(M+H)^+$; $^1$H NMR (400 MHz, $CDCl_3$): 1.02 (t, J=7.2 Hz, 3H), 1.76 (m, 2H), 2.46 (d, J=11.6 Hz, 1H), 2.56 (m, 1H), 2.68 (m, 1H), 3.28 (d, J=15.2 Hz, 1H), 3.35 (d, J=11.6 Hz, 1H), 3.80 (d, J=15.2 Hz, 1H), 3.95 (s, 3H), 4.08 (s, 3H), 4.11 (s, 3H), 4.13 (s, 3H), 5.03 (s, 1H), 6.67 (s, 1H), 7.60 (s, 1H), 7.68 (s, 1H), 7.76 (s, 1H). $^{13}$C NMR (150 MHz, $CDCl_3$): 12.0, 19.7, 54.0, 55.8, 55.9, 56.0, 58.0, 60.4, 64.7, 102.9, 103.0, 104.9, 123.0, 123.8, 124.2, 125.3, 126.7, 127.3, 148.3, 148.5, 148.7, 148.8.

Compound 14:

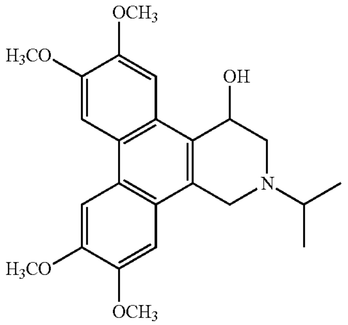

Yellow crystal; mp 170~172° C.; MS (ES, positive mode): m/z 412 $(M+H)^+$; $^1$H NMR (300 MHz, $CDCl_3$): 1.25 (m, 6H), 2.68 (d, J=11.7 Hz, 1H), 3.14 (m, 1H), 3.31 (d, J=11.7 Hz, 1H), 3.89 (d, J=15.3 Hz, 1H), 4.04 (s, 3H), 4.05 (s, 3H), 4.07 (s, 3H), 4.08 (s, 3H), 4.23 (d, J=15.3 Hz, 1H), 5.14 (s, 1H), 7.12 (s, 1H), 7.70 (s, 1H), 7.79 (s, 1H), 7.81 (s, 1H). $^{13}$C NMR (150 MHz, $CDCl_3$): 17.4, 19.5, 50.3, 52.8, 53.9, 55.9, 56.0, 56.1, 64.6, 103.1, 103.2, 103.3, 104.6, 123.6, 123.9, 124.4, 125.4, 127.4, 128.2, 148.6, 148.7, 149.0, 149.1.

Compound 18:

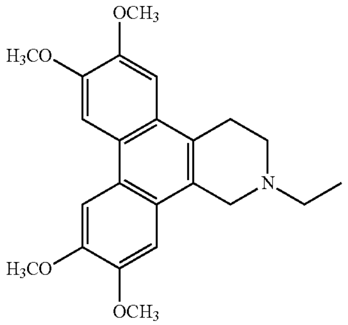

White crystal; mp 186° C.; MS (ES, positive mode): m/z 382 $(M+H)^+$; $^1$H NMR (400 MHz, $CDCl_3$): 1.31 (t, J=7.2 Hz, 3H), 2.81 (quartet, J=7.2 Hz, 2H), 2.96 (t, J=5.6 Hz, 2H), 3.22 (t, J=5.6 Hz, 2H), 4.02 (s, 2H), 4.04 (s, 3H), 4.05 (s, 3H), 4.12 (s, 6H), 7.15 (s, 1H), 7.29 (s, 1H), 7.82 (s, 1H), 7.83 (s, 1H); $^{13}$C NMR (75 MHz, $CDCl_3$): 12.2, 26.7, 49.4, 52.0, 53.4, 55.8, 55.9, 56.9, 102.8, 103.3, 103.4, 103.8, 123.4, 123.5, 124.1, 124.7, 125.5, 125.6, 148.4, 148.5, 148.7.

Compound 19:

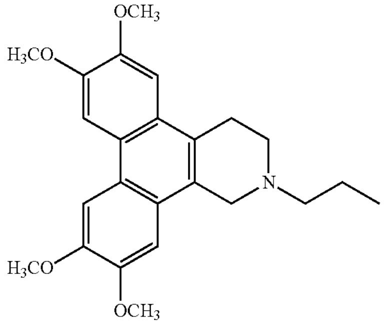

White crystal; mp 176~178° C.; MS (ES, positive mode): m/z 396 $(M+H)^+$; $^1$H NMR (400 MHz, $CDCl_3$): 1.02 (t, J=7.6 Hz, 3H), 1.74 (sextet, J=7.6 Hz, 2H), 2.67 (t, J=7.6 Hz, 2H), 2.92 (t, J=6.0 Hz, 2H), 3.18 (t, J=6.0 Hz, 2H), 3.98 (s, 2H), 4.03 (s, 3H), 4.04 (s, 3H), 4.10 (s, 6H), 7.12 (s, 1H), 7.27 (s, 1H), 7.79 (s, 1H), 7.80 (s, 1H); $^{13}$C NMR (100 MHz, $CDCl_3$): 12.0, 20.5, 27.2, 50.1, 54.3, 55.8, 55.9, 56.0, 60.6, 102.9, 103.2, 103.4, 103.8, 123.3, 123.4, 124.3, 125.6, 125.9, 148.3, 148.4, 148.6.

Compound 20:

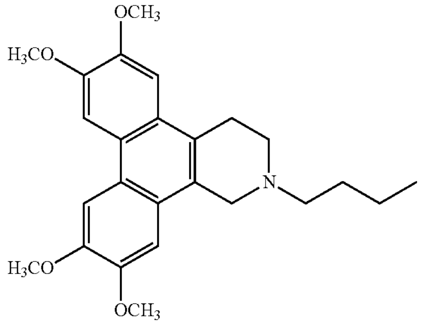

White needle; mp 172~173° C.; MS (ES, positive mode): m/z 410 $(M+H)^+$. $^1$H NMR (300 MHz, $CDCl_3$): 1.00 (t, J=7.5 Hz, 3H), 1.45 (sextet, J=7.5 Hz, 2H), 1.70 (quintet, J=7.5 Hz, 2H), 2.70 (t, J=7.5 Hz, 2H), 2.91 (t, J=5.7 Hz, 2H), 3.18 (t, J=5.7 Hz, 2H), 3.97 (s, 2H), 4.03 (s, 3H), 4.04 (s, 3H), 4.10 (s, 6H), 7.12 (s, 1H), 7.26 (s, 1H), 7.79 (s, 1H), 7.80 (s, 1H). $^{13}$C NMR (75 MHz, $CDCl_3$): 14.1, 20.8, 27.2, 29.4, 50.1, 54.3, 55.8, 55.9, 58.4, 102.8, 103.2, 103.3, 103.8, 123.3, 123.4, 124.2, 125.6, 125.9, 148.2, 148.3, 148.5, 148.6.

Compound 21:

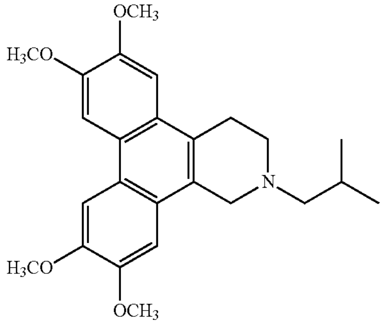

Light yellow needle; mp 160~161° C.; MS (ES, positive mode): m/z 410 $(M+H)^+$; $^1$H NMR (300 MHz, $CDCl_3$): 1.02 (d, J=6.6 Hz, 6H), 2.04 (septet, J=6.9 Hz, 1H), 2.47 (d, J=7.5 Hz, 2H), 2.90 (t, J=6.0 Hz, 2H), 3.18 (t, J=6.0 Hz, 2H), 3.97 (s, 2H), 4.03 (s, 3H), 4.04 (s, 3H), 4.11 (s, 6H), 7.13 (s, 1H), 7.29 (s, 1H), 7.80 (s, 1H), 7.81 (s, 1H); $^{13}$C NMR (75 MHz, $CDCl_3$): 21.0, 25.8, 27.1, 50.2, 54.8, 55.8, 55.9, 56.0, 66.8, 102.9, 103.2, 103.4, 103.8, 123.3, 123.4, 124.3, 125.6, 125.8, 126.0, 148.3, 148.4, 148.6.

Compound 23:

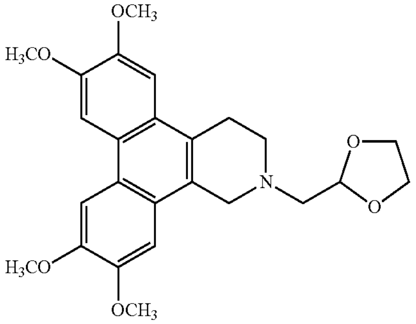

White needle; mp 182~183° C.; MS (ES, positive mode): m/z 440 $(M+H)^+$; $^1H$ NMR (300 MHz, $CDCl_3$): 2.96 (d, J=4.2 Hz, 2H), 3.07 (t, J=5.1 Hz, 2H), 3.19 (t, J=5.1 Hz, 2H), 3.91 (AA'BB', 2H), 4.02 (s, 3H), 4.03 (s, 3H), 4.04 (AA'BB', 2H), 4.10 (s, 6H), 4.12 (s, 2H), 5.21 (t, J=4.5 Hz, 1H), 7.12 (s, 1H), 7.26 (s, 1H), 7.79 (s, 1H), 7.80 (s, 1H); $^{13}C$ NMR (75 MHz, $CDCl_3$): 26.9, 51.0, 54.7, 55.8, 55.9, 60.9, 64.9, 102.9, 103.2, 103.3, 103.8, 123.3, 123.4, 124.2, 125.5, 125.7, 148.3, 148.4, 148.6.

Compound 24:

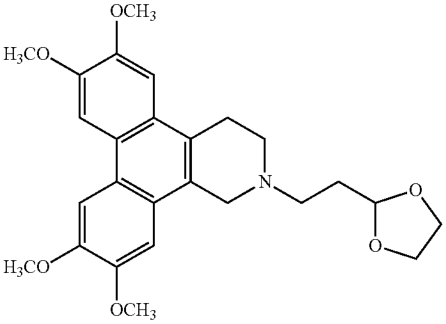

White crystal; mp 186~187° C.; MS (ES, positive mode): m/z 454 $(M+H)^+$; $^1H$ NMR (300 MHz, $CDCl_3$): 2.10 (td, J=7.5, 4.5 Hz, 2H), 2.87 (t, J=7.5 Hz, 2H), 2.94 (t, J=5.7 Hz, 2H), 3.18 (t, J=5.7 Hz, 2H), 3.88 (AA'BB', 2H), 3.99 (s, 2H), 4.02 (AA'BB', 2H), 4.03 (s, 6H), 4.10 (s, 6H), 5.04 (t, J=4.8 Hz, 1H), 7.10 (s, 1H), 7.26 (s, 1H), 7.79 (s, 1H), 7.80 (s, 1H). $^{13}C$ NMR (75 MHz, $CDCl_3$): 27.2, 31.7, 50.1, 53.3, 54.2, 55.8, 55.9, 56.0, 64.9, 102.8, 102.9, 103.2, 103.3, 103.4, 103.8, 123.3, 123.4, 124.2, 125.4, 125.5, 125.8, 148.3, 148.4, 148.6.

Compound 25:

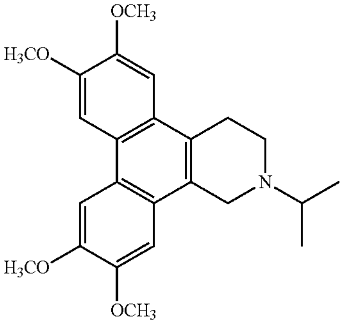

White needle; mp 185° C.; MS (ES, positive mode): m/z 396 $(M+H)^+$; $^1H$ NMR (300 MHz, $CDCl_3$): 1.26 (d, J=6.6 Hz, 6H), 2.95 (t, J=5.7 Hz, 2H), 3.09 (septet, J=6.6 Hz, 1H), 3.17 (t, J=5.7 Hz, 2H), 4.03 (s, 3H), 4.04 (s, 3H), 4.08 (s, 2H), 4.10 (s, 6H), 7.13 (s, 1H), 7.27 (s, 1H), 7.80 (s, 1H), 7.81 (s, 1H). $^{13}C$ NMR (75 MHz, $CDCl_3$): 18.5, 27.8, 45.1, 49.9, 54.1, 55.8, 55.9, 102.9, 103.2, 103.4, 103.8, 123.3, 124.4, 125.7, 126.1, 148.2, 148.3, 148.5.

Compound 26:

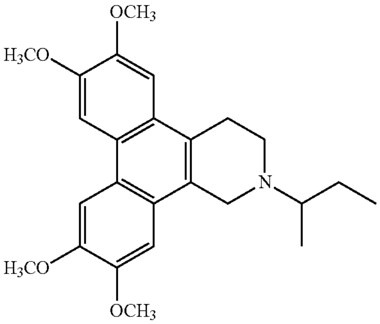

Light yellow crystal; mp 157~158° C.; MS (ES, positive mode): m/z 410 $(M+H)^+$; $^1H$ NMR (300 MHz, $CDCl_3$): 1.00 (t, J=7.5 Hz, 3H), 1.19 (d, J=6.3 Hz, 3H), 1.50 (m, 1H), 1.81 (m, 2H), 2.85 (m, 1H), 2.97 (m, 1H), 3.15 (t, J=5.4 Hz, 2H), 4.03 (s, 3H), 4.04 (s, 3H), 4.08 (s, 2H), 4.10 (s, 6H), 7.13 (s, 1H), 7.27 (s, 1H), 7.78 (s, 1H), 7.80 (s, 1H). $^{13}C$ NMR (75 MHz, $CDCl_3$): 11.5, 13.8, 26.3, 28.0, 29.6, 44.8, 49.8, 55.8, 55.9, 60.4, 102.9, 103.2, 103.3, 103.8, 123.3, 124.4, 125.8, 126.3, 126.5, 148.2, 148.3, 148.5.

Compound 29

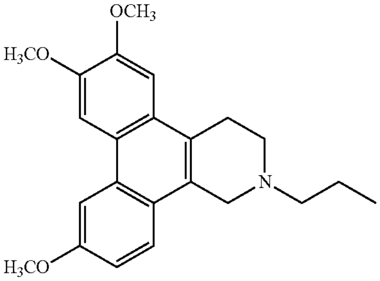

$^1H$-NMR (400 MHz, $CDCl_3$): 1.02 (3H, t, J=7.6 Hz), 1.74 (2H, sextet, J=7.6 Hz), 2.66 (2H, t, J=7.6 Hz), 2.93 (2H, t, J=6.0 Hz), 3.19 (2H, t, J=6.0 Hz), 4.02 (3H, s), 4.05 (5H, s), 4.11 (3H, s), 7.20 (1H, dd, J=8.8 Hz, J=2.4 Hz), 7.30 (1H, s), 7.81 (1H, d, J=8.8 Hz), 7.90 (1H, d, J=2.4 Hz), 7.91 (1H, s).

Compound 30:

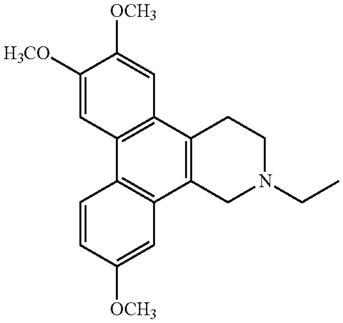

Yellow crystal; mp 111~112° C.; MS (ES, positive mode): m/z 352 $(M+H)^+$; $^1H$ NMR (300 MHz, $CDCl_3$): 1.31 (t, J=7.2 Hz, 3H), 2.79 (q, J=7.2 Hz, 2H), 2.95 (t, J=5.7 Hz, 2H), 3.23 (t, J=5.7 Hz, 2H), 3.97 (s, 3H), 4.01 (s, 2H), 4.04 (s, 3H), 4.10 (s, 3H), 7.21 (dd, J=8.9, 2.6 Hz, 1H), 7.24 (d, J=2.6 Hz, 1H), 7.30 (s, 1H), 7.93 (s, 1H), 8.46 (d, J=8.9 Hz, 1H).

Compound 31

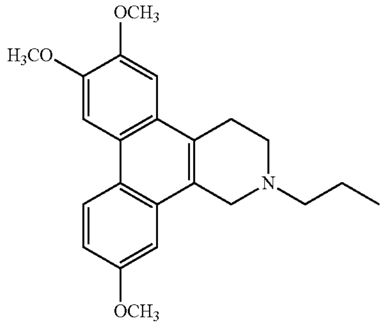

$^{1}$H-NMR (300 MHz, $CDCl_3$): 1.02 (3H, t, J=7.5 Hz), 1.75 (2H, sextet, J=7.5 Hz), 2.68 (2H, t, J=7.5 Hz), 2.94 (2H, t, J=6.0 Hz), 3.22 (2H, t, J=6.0 Hz), 3.97 (3H, s), 4.00 (2H, s), 4.04 (3H, s), 4.10 (3H, s), 7.21 (1H, dd, J=8.7 Hz, J=2.7 Hz), 7.25 (1H, d, J=2.7 Hz), 7.30 (1H, s), 7.93 (1H, s), 8.46 (1H, d, J=10.4 Hz).

Compound 32

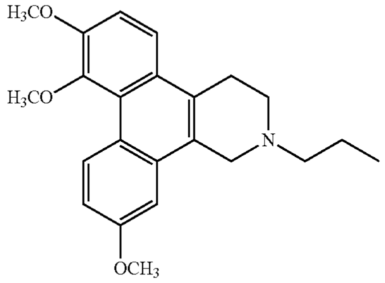

$^{1}$H-NMR (300 MHz, $CDCl_3$): 1.01 (3H, t, J=7.5 Hz), 1.74 (2H, sextet, J=7.5 Hz), 2.66 (2H, t, J=7.8 Hz), 2.90 (2H, t, J=5.7 Hz), 3.21 (2H, t, J=5.7 Hz), 3.89 (3H, s), 3.96 (2H, s), 3.98 (3H, s), 4.02 (3H, s), 7.21 (1H, d, J=2.9 Hz), 7.24 (1H, dd, J=10.4 Hz, J=2.9 Hz), 7.27 (1H, d, J=9.0 Hz), 7.75 (1H, d, J=9.0 Hz), 9.62 (1H, d, J=8.7 Hz).

Compound 33:

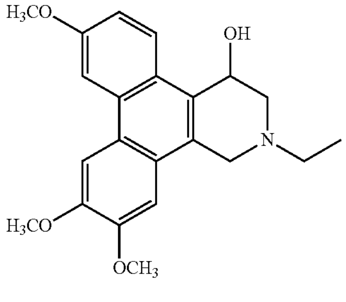

Yellow needle; mp 207~208° C.; MS (ES, positive mode): m/z 368 $(M+H)^+$; $^{1}$H NMR (300 MHz, $CDCl_3$): 1.28 (t, J=7.2 Hz, 3H), 2.38 (dd, J=11.4, 2.4 Hz, 1H), 2.60 (ddq, J=14.7, 12.3, 7.2 Hz, 1H), 2.78 (ddq, J=14.7, 12.3, 7.2 Hz, 1H), 3.18 (d, J=14.7 Hz, 1H), 3.36 (d, J=11.4 Hz, 1H), 3.62 (d, J=14.7 Hz, 1H), 3.91 (s, 3H), 4.03 (s, 3H), 4.10 (s, 3H), 5.05 (s, 1H), 6.53 (s, 1H), 7.24 (dd, J=9.3, 2.7 Hz, 1H), 7.72 (d, J=2.7 Hz, 1H), 8.34 (d, J=9.3 Hz, 1H).

Compound 34:

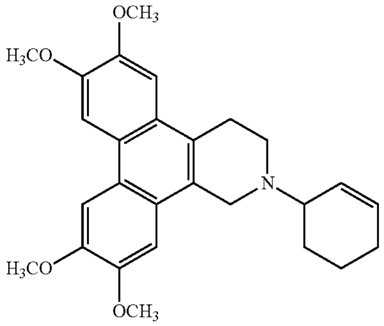

Light yellow crystal; mp 128~129° C.; MS (APCI, positive mode): m/z 434 $(M+H)^+$; $^{1}$H NMR (400 MHz, $CDCl_3$): 1.67 (m, 1H), 1.76 (m, 1H), 1.93 (m, 1H), 2.02 (m, 1H), 2.08 (m, 2H), 2.93 (m, 1H), 3.07 (m, 1H), 3.17 (t, J=5.2 Hz, 2H), 3.63 (br s, 1H), 4.03 (s, 3H), 4.04 (s, 3H), 4.10 (s, 6H), 4.16 (d, J=6.0 Hz, 2H), 5.86 (d, J=10.4 Hz, 1H), 5.95 (d, J=10.4 Hz, 1H), 7.12 (s, 1H), 7.27 (s, 1H), 7.80 (s, 1H), 7.81 (s, 1H). $^{13}$C NMR (100 MHz, $CDCl_3$): 21.7, 23.2, 25.4, 28.0, 45.2, 49.9, 55.8, 56.0, 60.0, 103.0, 103.2, 103.4, 103.9, 123.3, 123.4, 124.4, 125.8, 126.2, 126.3, 129.2, 130.6, 148.3, 148.4, 148.6.

Compound 35:

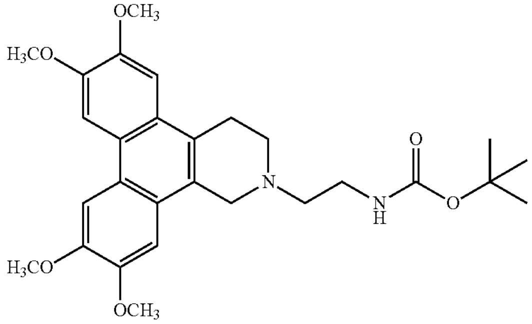

Yellow crystal; mp 123~124° C.; MS (ES, positive mode): m/z 497 $(M+H)^+$; $^{1}$H NMR (300 MHz, $CDCl_3$): 1.43 (s, 9H), 2.84 (t, J=5.7 Hz, 2H), 2.94 (t, J=5.7 Hz, 2H), 3.19 (t, J=5.4 Hz, 2H), 3.44 (quartet, J=5.7 Hz, 2H), 4.00 (s, 2H), 4.04 (s, 6H), 4.11 (s, 6H), 5.20 (br s, 1H), 7.10 (s, 1H), 7.28 (s, 1H), 7.80 (s, 1H), 7.81 (s, 1H). $^{13}$C NMR (75 MHz, $CDCl_3$): 27.2, 28.4, 49.9, 54.0, 54.8, 55.8, 55.9, 56.0, 57.1, 102.8, 103.3, 103.4, 103.8, 123.4, 123.5, 124.1, 125.3, 125.5, 125.9, 148.4, 148.6, 148.7.

Compound 36:

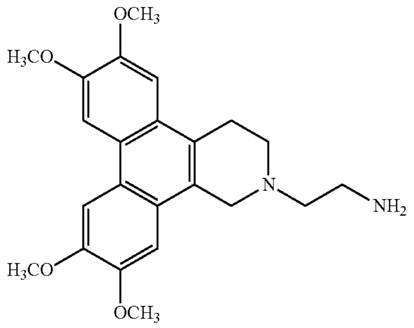

Colorless rock; mp 161~162° C.; MS (ES, positive mode): m/z 397 $(M+H)^+$; $^1H$ NMR (300 MHz, $CDCl_3$): 2.80 (t, J=6.0 Hz, 2H), 2.94 (t, J=6.0 Hz, 2H), 2.99 (t, J=6.0 Hz, 2H), 3.19 (t, J=5.7 Hz, 2H), 4.02 (s, 2H), 4.04 (s, 6H), 4.11 (s, 6H), 7.13 (s, 1H), 7.28 (s, 1H), 7.81 (s, 1H), 7.82 (s, 1H).

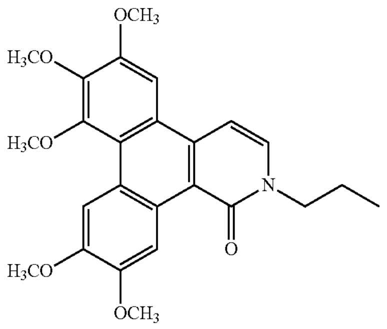 [SMILES: CCCn1ccc2c3cc(OC)c(OC)c(OC)c3c3cc(OC)c(OC)cc3c2c1=O]

$^1H$-NMR (300 MHz, $CDCl_3$): 1.04 (3H, t, J=7.2 Hz), 1.92 (2H, sextet, J=7.2 Hz), 3.93 (3H, s), 4.09 (3H, s), 4.10 (3H, s), 4.11 (3H, s), 4.14 (2H, m), 4.16 (3H, s), 7.21 (1H, d, J=7.9 Hz), 7.39 (1H, d, J=7.9 Hz), 7.66 (1H, s), 9.23 (1H, s), 10.11 (1H, s).

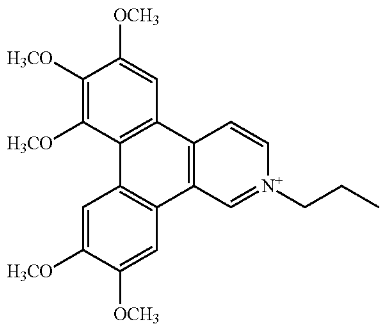 [SMILES: CCC[n+]1ccc2c(c1)c1cc(OC)c(OC)cc1c1c(OC)c(OC)c(OC)cc21]

$^1H$-NMR (400 MHz, $CDCl_3$): 1.01 (3H, t, J=7.2 Hz), 2.07 (2H, m), 3.83 (3H, s), 4.06 (3H, s), 4.09 (3H, s), 4.13 (3H, s), 4.36 (3H, s), 5.22 (2H, s), 7.58 (1H, s), 8.42 (1H, s), 8.69 (1H, s), 8.80 (2H, s), 10.89 (1H, s).

EXAMPLE 2

Inhibition of NO production

Inhibition of Nitric Oxide Production

RAW 264.7 cells were seeded (70,000 cells/well) and cultured in a 96-well culture plate using the DMEM medium described above. 24 hours later, the medium was replaced with a fresh DMEM medium supplemented with LPS (10 μg/ml)/IFNγ (20 ng/ml). Test compounds (at different concentrations) were then added. The cells, incubated with or without test compounds, were then cultured for 18-24 h and the nitrate and nitric oxide levels in the culturing medium were measured using a Nitrate/Nitrite assay kit (Cayman Chemical). Nitrate was reduced to nitrite with nitrate reductase and determined spectrophotometrically with Griess reagent at $OD_{540}$. For each test compound, a dose-response curve was drawn based on the concentrations of the compound versus the corresponding nitrate/nitric oxide levels in the culturing media of the cells treated with the compound. The $EC_{50}$ value of that compound for inhibiting nitric oxide production was determined according to the dose-response curve.

Results show that all of Compounds 1-36 inhibited NO production. Some of the compounds, e.g., Compounds 1, 9, 10, 14, 25, and 33 had $EC_{50}$ values lower than 1 μM.

EXAMPLE 3

Inhibition of Cancer Cell Growth

NCI H460 (human lung cancer cell line), MCF7 (human breast cancer cell line), SF268 (human brain cancer cell line), HONE-1 (human nasopharyngeal epithelial carcinomas cell line), NUGC-3 (human gastric cancer cell line) cells, HepG2 (human hepatocellular carcinoma cell line), and A549 (human lung adenocarcinoma epithelial cell line) were maintained in DMEM medium containing 10% fetal bovine serum, seeded in 96-well plates (2500, 6500, 7500, 4500, 6000, 10000, or 5000 cells/well), and incubated at 37° C. with 5% $CO_2$ supply for 24 h. The cells were then incubated with or without a test compound (at five different concentrations) in a $CO_2$ incubator at 37° C. for 72 h. The number of viable cells in each well was determined by the tetrazolium dye reduction assay (MTS assay) according to the protocol provided by the manufacturer (Promega, Madison, Wis., USA). For each test compound, a dose-response curve was drawn based on the concentrations of the compound versus the numbers of viable cells treated with the compound at those concentrations. The $CC_{50}$ value of that compound, referring to the concentration of the compound required to reduce the cancer cell growth by 50%, was determined according to the dose-response curve.

Compounds 1-36 were tested in this assay. They all show inhibitory effect against the tested cancer cells (having $CC_{50}$ values lower than 50 μM). Unexpectedly, some of these compounds had $CC_{50}$ values lower than 1

EXAMPLE 4

Inhibition of Transmissible Gastroenteritis Virus (TGEV) Protein Production

Swine testicular (ST) cells were cultured in a 96-well plate in the presence or absence of a test compound (at 8 different concentrations) for 2 hours and then infected with TGEV at a MOI of 10. Six hours after TGEV infection, the ST cells were fixed with 80% acetone and subjected to an indirect immunofluorescent assay (IFA) to examine the levels of TGEV spike (S) and nucleocapsid (N) proteins. Briefly, the fixed cells were incubated with murine monoclonal antibodies specific to these two viral proteins for a sufficient period to allow binding of the antibodies to the viral proteins. After being washed with phosphate-buffered saline for three times, the cells were incubated with a fluorescein isothiocyanate-conjugated anti-mouse immunoglobulin antibody (ICN Pharmaceuticals, Inc./Cappel) for 60 min at room temperature. The cells were washed again with phosphate-buffered saline for three times, and the fluorescence intensities released from these cells were measured by a Wallac Victor II system (Packard, Inc.) at excitation and emission wavelengths 485 nm and 535 nm, respectively. The 50% effective concentration ($EC_{50}$) for inhibiting S and N protein expression of the test compound was determined based on the florescence intensity values thus measured. Alternatively, the fluorescence intensities were detected by fluorescence microscopy. More specifically, the fluorescent images produced under 485 nm and 535 nm were captured by a charge-coupled device linked to a Leica IM50 Image Manager.

Compounds 1, 2, 4-10, 14, 18, 19, and 25-33 were tested in the assay described above. Almost all of these compounds showed $EC_{50}$ values below 10 μM. Among them, Compounds 1, 2, 4-6, 8-10, 19, 25, and 26 showed $EC_{50}$ values lower than 1 μM.

In sum, the results indicate that these test compounds effectively inhibited production of TGEV viral proteins, thereby suppressing viral replication.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention can be made and used to practice this invention. Thus, other embodiments are also within the claims.

What is claimed is:

1. A compound of the following formula:

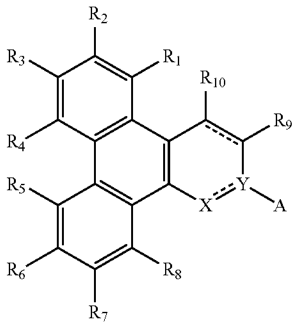

wherein each of $R_1$, $R_2$, $R_3$, $R_4$, $R_5$, $R_6$, $R_7$, $R_8$, $R_9$, and $R_{10}$, independently, is H, alkyl, alkenyl, alkynyl, cycloalkyl, heterocycloalkyl, aryl, heteroaryl, halo, nitro, cyano, —$OR^a$, —$OC(O)R^a$, —$C(O)OR^a$, —$NR^aR^b$, —$NR^aC(O)R^b$, or —$C(O)NR^aR^b$, each of $R^a$ and $R^b$, independently, being H, alkyl, aryl, heteroaryl, cycloalkyl, or hetercycloalkyl;

at least one of $R_1$-$R_8$ is $OR^a$;

X ==== Y, together, are C(R')(R")—N, in which R' is H, alkyl, alkenyl, alkynyl, cycloalkyl, heterocycloalkyl, aryl, heteroaryl, halo, nitro, or cyano, and R" is H, alkyl, alkenyl, alkynyl, cycloalkyl, heterocycloalkyl, aryl, heteroaryl, halo, nitro, cyano, —$OR^c$, or —$OC(O)R^c$, $R^c$ being H, alkyl, aryl, heteroaryl, cycloalkyl, or hetercycloalkyl;

==== is a single bond; and

A is H, alkyl, alkenyl, alkynyl, cycloalkyl, heterocycloalkyl, aryl, or heteroaryl.

2. The compound of claim 1, wherein A is alkyl.

3. The compound of claim 2, wherein A is $CH_2CH_3$, $(CH_2)_2CH_3$, or $CH(CH_3)_2$.

4. The compound of claim 2, wherein A is alkyl substituted with one or more groups selected from halo, alkenyl, alkynyl, aryl, heteroaryl, cycloalkyl, heterocycloalkyl, nitro, cyano, —$OR^d$, —$OC(O)R^d$, —$C(O)OR^d$, —$NR^dR^e$, —$NR^dC(O)R^e$, or —$C(O)NR^dR^e$, each of $R^d$ and $R^e$, independently, being H, alkyl, cycloalkyl, hetercycloalkyl, aryl, or heteroaryl.

5. The compound of claim 4, wherein A is $C_{2-3}$ alkyl substituted with OH.

6. The compound of claim 1, wherein the compound is

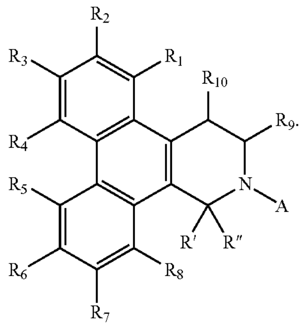

7. The compound of claim 6, wherein A is alkyl.

8. The compound of claim 7, wherein A is $CH_2CH_3$, $(CH_2)_2CH_3$, or $CH(CH_3)_2$.

9. The compound of claim 7, wherein A is alkyl substituted with one or more groups selected from halo, alkenyl, alkynyl, aryl, heteroaryl, cycloalkyl, heterocycloalkyl, nitro, cyano, —$OR^d$, —$OC(O)R^d$, —$C(O)OR^d$, —$NR^dR^e$, —$NR^dC(O)R^e$, or —$C(O)NR^dR^e$, each of $R^d$ and $R^e$, independently, being H, alkyl, cycloalkyl, hetercycloalkyl, aryl, or heteroaryl.

10. The compound of claim 9, wherein A is $C_{2-3}$ alkyl substituted with OH.

11. The compound of claim 1, wherein each of $R_6$ and $R_7$ is —$OR^a$, in which $R^a$ is H or alkyl.

12. The compound of claim 11, wherein $R_3$ is —$OR^a$, in which $R^a$ is H or alkyl.

13. The compound of claim 6, wherein each of $R_6$ and $R_7$ is —$OR^a$, in which $R^a$ is H or alkyl.

14. The compound of claim 13, wherein $R_3$ is —$OR^a$, in which $R^a$ is H or alkyl.

15. The compound of claim 14, wherein A is alkyl.

16. The compound of claim 15, wherein A is $CH_2CH_3$, $(CH_2)_2CH_3$, or $CH(CH_3)_2$.

17. The compound of claim 15, wherein A is alkyl substituted with one or more groups selected from halo, alkenyl, alkynyl, aryl, heteroaryl, cycloalkyl, heterocycloalkyl, nitro, cyano, —$OR^d$, —$OC(O)R^d$, —$C(O)OR^d$, —$NR^dR^e$, —$NR^dC(O)R^e$, or —$C(O)NR^dR^e$, each of $R^d$ and $R^e$, independently, being H, alkyl, cycloalkyl, hetercycloalkyl, aryl, or heteroaryl.

18. The compound of claim 17, wherein A is $C_{2-3}$ alkyl substituted with OH.

19. The compound of claim 18, wherein each of R' and R" is H and $R_{10}$ is OH.

20. The compound of claim 6, wherein each of R' and R" is H and $R_{10}$ is OH.

21. The compound of claim 1, wherein the compound is selected from the group consisting of:

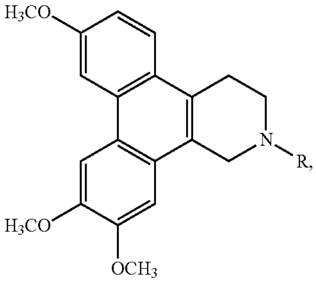
R = —$CH_2CH_3$,
—$(CH_2)_2CH_3$,
—$(CH_2)_3CH_3$
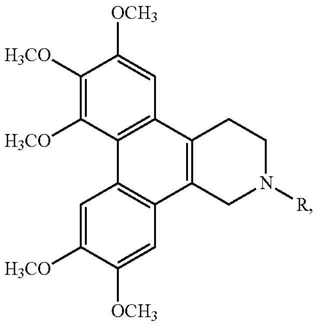
R = —$CH_2CH_3$,
—$(CH_2)_2CH_3$,
—$(CH_2)_3CH_3$, or
—$CH(CH_3)_2$
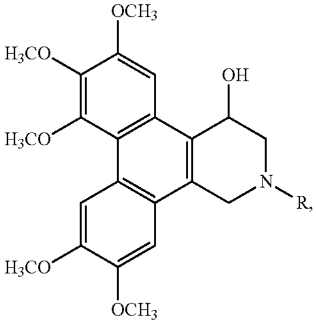
R = —$(CH_2)_2CH_3$
-continued
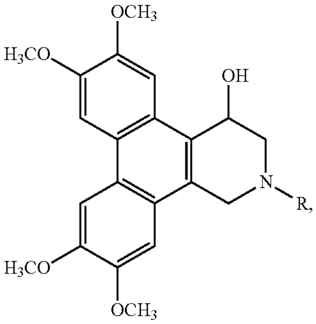
R = —$CH_2CH_3$,
—$(CH_2)_2CH_3$,
—$(CH_2)_3CH_3$,
—$CH_2CH(CH_3)_2$
—$(CH_2)_4CH_3$,
—$CH(CH_3)_2$,
—$CH(CH_3)CH_2CH_3$,
—$(CH_2)_3OTHP$, or
—$(CH_2)_3OH$
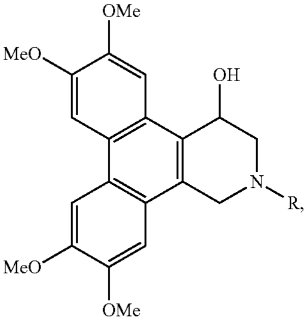
R = —$CH_2CH_3$,
—$(CH_2)_2CH_3$,
—$(CH_2)_3CH_3$,
—$CH_2CH(CH_3)_2$
—$(CH_2)_4CH_3$,
-2-methyl-[1,3]dioxolane,
-2-ethyl-[1,3]dioxolane,
—$CH(CH_3)_2$,
—$CH(CH_3)CH_2CH_3$,
—$(CH_2)_3OTHP$, or
—$(CH_2)_3OH$
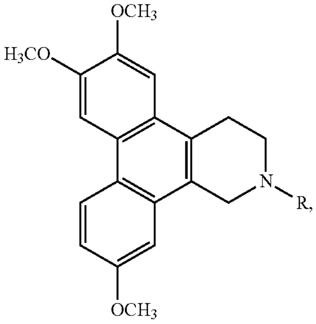
R = —$CH_2CH_3$, or
—$(CH_2)_2CH_3$ -continued

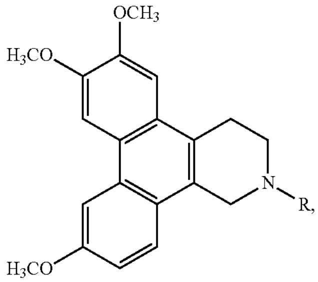

R = $-(CH_2)_2CH_3$

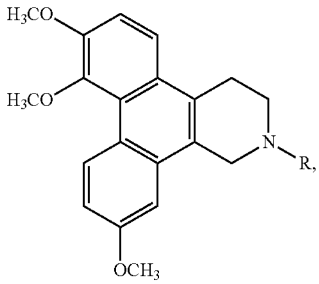

and

R = $-(CH_2)_2CH_3$

-continued

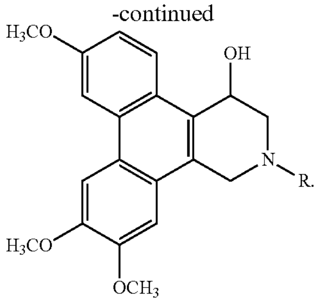

R = $-CH_2CH_3$

22. A method of treating an inflammatory disease caused by nitric oxide overproduction from iNOS, comprising administering to a subject in need thereof an effective amount of a compound of claim 1.

23. The method of claim 22, wherein the inflammatory disease is arthritis.

24. A method of treating cancer, comprising administering to a subject in need thereof an effective amount of a compound of claim 1 wherein the cancer is selected from the group consisting of lung cancer, breast cancer, nasopharyngeal epithelial carcinomas cancer, gastric cancer, hepatocellular carcinoma cancer and lung adenocarcinoma epithelial cancer.

25. A method for treating coronavirus infection, comprising administering to a subject thereof an effective amount of a compound of claim 1.

26. The method of claim 25, wherein the coronavirus infection is caused by human CoV 229E, transmissible gastroenteritis virus, mouse hepatitis virus, bovine CoV, infectious bronchitis virus, Feline coronaviruses, or severe acute respiratory syndrome virus.

* * * * *